United States Patent
Li et al.

(10) Patent No.: US 9,817,149 B2
(45) Date of Patent: Nov. 14, 2017

(54) VEHICLE INSPECTION SYSTEM

(71) Applicants: TSINGHUA UNIVERSITY, Beijing (CN); NUCTECH COMPANY LIMITED, Beijing (CN)

(72) Inventors: Jianmin Li, Beijing (CN); Ying Li, Beijing (CN); Yuanjing Li, Beijing (CN); Yulan Li, Beijing (CN); Tao Song, Beijing (CN); Yu Hu, Beijing (CN); Yucheng Wu, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 264 days.

(21) Appl. No.: 14/582,079

(22) Filed: Dec. 23, 2014

(65) Prior Publication Data
US 2016/0054469 A1 Feb. 25, 2016

(30) Foreign Application Priority Data

Aug. 22, 2014 (CN) .......................... 2014 1 0418956

(51) Int. Cl.
*G01N 23/04* (2006.01)
*G01V 5/00* (2006.01)
*G01N 23/083* (2006.01)

(52) U.S. Cl.
CPC .......... *G01V 5/0016* (2013.01); *G01N 23/083* (2013.01)

(58) Field of Classification Search
CPC ............. G01N 23/083; G01N 23/2252; G01N 1/2202; G01N 1/405; G01N 2001/025;
(Continued)

(56) References Cited

U.S. PATENT DOCUMENTS 5,506,410 A * 4/1996 Sakurai ................ G02B 6/4246
250/227.11
6,542,580 B1 4/2003 Carver et al.
(Continued)

FOREIGN PATENT DOCUMENTS

CA 2 642 915 A1 4/2010
CA 2642915 A1 4/2010
(Continued)

OTHER PUBLICATIONS

International Search Report for PCT/CN2014/094614 dated Apr. 17, 2015, 6 pages.
(Continued)

*Primary Examiner* — Irakli Kiknadze
(74) *Attorney, Agent, or Firm* — Kilpatrick Townsend & Stockton LLP

(57) ABSTRACT

The present invention discloses a vehicle inspection system, comprising: a radiation source;
an inspection passage enabling a vehicle to pass; a dragging system comprising a first dragging means and a second dragging means, which are sequentially arranged along a vehicle dragging direction; in the vehicle dragging direction, the first dragging means is arranged at the upstream of the second dragging means, and a separating section is arranged between the first dragging means and the second dragging means, so that the first dragging means is separated from the second dragging means by a preset distance in the vehicle dragging direction; and the first and second dragging means both include a supporting plate, an elongated traction element and a pushing element connected with the elongated traction element, the elongated traction elements of the first and second dragging means are continuous and integrated, thus the elongated traction elements and pushing elements extends on the separat-
(Continued)

ing section; the supporting plates of the first and second dragging means are separated and two pieces type, and no supporting plate is provided on the separating section.

19 Claims, 13 Drawing Sheets

(58) Field of Classification Search
CPC ........... G01N 2033/0081; G01N 21/90; G01N 21/9018; G01N 21/9027; G01N 21/94; G01N 21/95; G01N 2201/0833; G01N 2223/204; G01N 2223/419; G01N 23/046; G01N 2223/423; G01N 2001/022; G01N 21/954; G01N 2223/637; G01N 2223/639; G01N 23/10; G01N 2021/9544; G01N 2021/95676; G01N 21/21; G01N 21/8806; G01N 21/9501; G01N 21/956; G01N 21/95607; G01V 5/0016; G01V 5/005; G01V 5/0025; H01L 2924/00; H01L 2224/73265; H01L 2224/48227; H01L 2224/32145; H01L 2924/00012; H01L 2224/32225; H01L 2224/92247; H01L 2924/00014; H01L 2224/45015; H01L 2224/45144; H01L 2224/45147; H01L 2224/48145; H01L 2924/01
USPC .................................. 378/62, 57, 58, 70, 208
See application file for complete search history.

(56) References Cited

U.S. PATENT DOCUMENTS

| | | | | |
|---|---|---|---|---|
| 7,486,768 B2* | 2/2009 | Allman | ................ | G01V 5/0008 378/147 |
| 7,626,186 B2* | 12/2009 | Kang | ..................... | A61L 2/087 204/157.44 |
| 7,692,650 B2* | 4/2010 | Ying | ....................... | A61B 6/482 345/424 |
| 2004/0258198 A1 | 12/2004 | Carver et al. | | |
| 2005/0169421 A1 | 8/2005 | Muenchau et al. | | |
| 2007/0280416 A1 | 12/2007 | Bendahan et al. | | |
| 2008/0089476 A1* | 4/2008 | Chen | .................... | G01V 5/0066 378/57 |
| 2009/0136004 A1* | 5/2009 | Hu | ....................... | G01V 5/0008 378/198 |
| 2010/0028099 A1* | 2/2010 | Sun | ........................ | G01N 23/04 410/67 |

FOREIGN PATENT DOCUMENTS

| | | |
|---|---|---|
| CN | 101633351 A | 1/2010 |
| CN | 102107777 A | 6/2011 |
| EP | 2 711 694 A1 | 3/2014 |
| GB | 2 420 682 A | 5/2006 |
| GB | 2420682 A | 5/2006 |
| WO | 2012/106730 A2 | 8/2012 |

OTHER PUBLICATIONS

The partial search report dated Jan. 15, 2016 for the corresponding EP application (14200189.0).

European Search Report and Written Opinion for EP 14200189 dated Apr. 19, 2016, 11 pages.

* cited by examiner

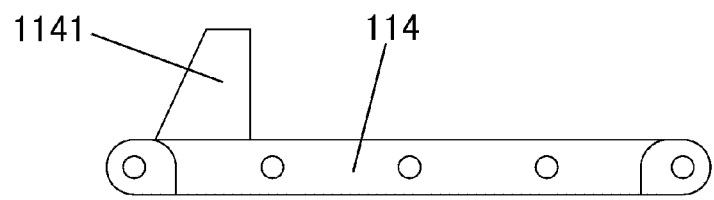
(A)
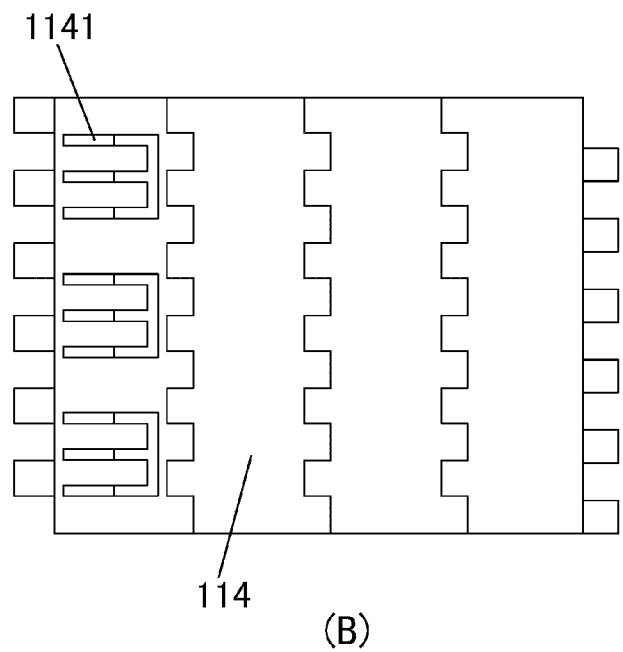
(B)
FIG. 20

VEHICLE INSPECTION SYSTEM

This application claims priority to Chinese Patent Application No. 201410418956.3, filed on Aug. 22, 2014, which is hereby incorporated by reference in its entirety.

FIELD OF INVENTION

The present invention relates to a vehicle inspection system.

BACKGROUND OF INVENTION

In a top-irradiation type vehicle inspection system, a radiation source is provided on the top of an inspection passage, a detector is provided on the bottom of the inspection passage. The inspected vehicle is typically driven to advance by chain type dragging means. The dragging means includes plate like carrier frame on the bottom, chain and pushing roller on the frame. In the power of motor, the inspected vehicle is moved by means of chain and pushing roller. Since supporting plates of the carrier frame is a metal structural, thus shielding ray beams when the vehicle is inspected. Consequently, the detector fails to obtain singles and meanwhile the obtained image is black, which severely influences the image quality and the inspection effect.

SUMMARY OF INVENTION

The objection of the present invention is to provide a vehicle inspection system, in order to ease or eliminate influence of dragging equipment on a scanned image.

According to one aspect of the present invention, a vehicle inspection system comprising: a radiation source; an inspection passage enabling a vehicle to pass; a dragging system comprising a first dragging means and a second dragging means, which are sequentially arranged along a vehicle dragging direction; in the vehicle dragging direction, the first dragging means is arranged at the upstream of the second dragging means, and a separating section is arranged between the first dragging means and the second dragging means, so that the first dragging means is separated from the second dragging means by a preset distance in the vehicle dragging direction; and the first and second dragging means both include a supporting plate, an elongated traction element and a pushing element connected with the elongated traction element, the elongated traction elements of the first and second dragging means are continuous and integrated, thus the elongated traction elements and pushing elements extends on the separating section; the supporting plates of the first and second dragging means are separated and two pieces type, and no supporting plate is provided on the separating section.

According to one aspect of the present invention, the invention provides a vehicle inspection system, comprising: a radiation source for providing X-ray beams for scanning a vehicle; a detector used for receiving the X-ray beams emitted from the radiation source; an inspection passage for enabling the vehicle to pass, wherein a scanning means frame is arranged within the range of the inspection passage, the radiation source is arranged at the top of the scanning means frame for scanning the vehicle passing the inspection passage, and the detector is arranged at a position opposite to the radiation source; a dragging system comprising a first dragging means and a second dragging means, which are sequentially arranged along a vehicle dragging direction; in the vehicle dragging direction, the first dragging means is arranged at the upstream of the second dragging means, and a separating section is arranged between the first dragging means and the second dragging means, so that the first dragging means is separated from the second dragging means by a preset distance in the vehicle dragging direction; and at least a part of paths of the beams of the radiation source passes through the separating section between the first dragging means and the second dragging means; the first and second dragging means both include a supporting plate, an elongated traction element and a pushing element connected with the elongated traction element, the elongated traction elements of the first and second dragging means are continuous and integrated, thus the elongated traction elements and pushing elements extends on the separating section; the supporting plates of the first and second dragging means are separated and two pieces type, and no supporting plate is provided on the separating section.

According to one aspect of the present invention, the vehicle inspection system further comprising: the dragging means is arranged on the ground at one side within the range of the inspection passage, and is able to drag the vehicle driving into the inspection passage to pass the inspection passage.

According to one aspect of the present invention, the width of the inspection passage is arranged in such a manner that the vehicle is able to pass the inspection passage by means of the dragging means, and the vehicle is also able to pass the inspection passage along the ground provided with no dragging means.

According to one aspect of the present invention, the vehicle inspection system further comprising: radiation shield walls arranged at the two sides of the inspection passage, a pedestrian passage arranged behind the radiation shield walls, for enabling a driver to walk from a starting point where the vehicle drives into the inspection passage to the destination where the vehicle is about to leave the inspection passage.

According to one aspect of the present invention, a vehicle inspection system, comprising: an inspection passage, a dragging system arranged in the inspection passage; and a radiographic inspection system for inspecting a vehicle, wherein the radiographic inspection system comprises a radiation source for emitting beams and a detector for receiving the beams emitted by the radiation source and penetrating through the inspected vehicle; a dragging system comprising a first dragging means and a second dragging means, which are sequentially arranged along a vehicle dragging direction; in the vehicle dragging direction, the first dragging means is arranged at the upstream of the second dragging means, and a separating section is arranged between the first dragging means and the second dragging means, so that the first dragging means is separated from the second dragging means by a preset distance in the vehicle dragging direction; and at least a part of paths of the beams of the radiographic inspection system passes through the separating section between the first dragging means and the second dragging means; the first and second dragging means both include a supporting plate, a elongated traction element and a pushing element connected with the elongated traction element, the elongated traction elements of the first and second dragging means are continuous and integrated, thus the elongated traction elements and pushing elements extends on the separating section; the supporting plates of the first and second dragging means are separated and two pieces type, and no supporting plate is provided on the separating section.

According to one aspect of the present invention, the pushing element is used for pushing wheels to move so as to drive the vehicle to advance.

According to one aspect of the present invention, the radiation source is arranged above the inspection passage.

According to one aspect of the present invention, the vehicle inspection system further comprising a driving passage arranged in the inspection passage and used for enabling the vehicle to voluntarily pass, wherein the driving passage is arranged to be substantially parallel to the dragging means.

According to one aspect of the present invention, the vehicle inspection system further comprising a controller, wherein the controller corrects an acquired image of the inspected vehicle according to a scanned image acquired by the vehicle inspection system during no load of the dragging means, in order to remove the image of the dragging means from the acquired image of the inspected vehicle.

According to one aspect of the present invention, the vehicle inspection system further comprising a controller, wherein the controller corrects an acquired image of the inspected vehicle according to a scanned image acquired by the vehicle inspection system during no load of the dragging means, in order to remove the image of at least one of the elongated traction element and the pushing element from the acquired image of the inspected vehicle.

According to one aspect of the present invention, the controller corrects the acquired image of the inspected vehicle according to the position relationship of the inspected vehicle and at least one of the elongated traction element and the pushing element along the vehicle transfer direction, in order to remove the image of at least one of the elongated traction element and the pushing element from the acquired image of the inspected vehicle.

According to one aspect of the present invention, the pushing element of the dragging means contacts the wheels of the vehicle and pushes the wheels, in order to determine the position relationship of the inspected vehicle and at least one of the elongated traction element and the pushing element along the vehicle transfer direction.

According to one aspect of the present invention, the vehicle inspection system further comprising: a position detecting means for detecting whether the pushing element arrives at a preset position, and sending a signal to the controller when the pushing element pushing the wheels of the vehicle or the pushing element during no load of the dragging means arrives at the preset position, in order to start the radiographic inspection system to scan the vehicle or the no-load dragging means.

According to one aspect of the present invention, the position detecting means is an optical transceiver, the optical transceiver is arranged at one side of the dragging means and emits a light beam towards one side of the dragging means, when the light beam irradiates a reflector at the end part of the pushing element, the optical transceiver receives the light beam reflected by the reflector at the end part of the pushing element, in order to determine that the pushing element arrives at the preset position.

According to one aspect of the present invention, the first dragging means comprises a first elongated traction element and a first pushing element connected with the first elongated traction element, and the first pushing element is adapted to push the wheels to move so as to drive the vehicle to advance; the second dragging means comprises a second elongated traction element and a second pushing element connected with the second elongated traction element, and the second pushing element is adapted to push the wheels to move so as to drive the vehicle to advance.

According to one aspect of the present invention, the vehicle passes the inspection passage under a first mode, a second mode or a third mode, under the first mode, the vehicle voluntarily passes the inspection passage, and the radiographic inspection system does not inspect the vehicle, under the second mode, the vehicle voluntarily passes the inspection passage, and the radiographic inspection system inspects the vehicle by adopting a dosage lower than a first preset value, and under the third mode, the dragging system drags the vehicle to pass the inspection passage, and the radiographic inspection system inspects the vehicle by adopting a dosage larger than or equal to a second preset value.

According to one aspect of the present invention, under the first mode and the second mode, the wheels of at least one side of the vehicle drive on the first dragging means and the second dragging means or the vehicle drives on a road beside the first dragging means and the second dragging means.

According to one aspect of the present invention, the pushing element is adapted to push the wheels to move so as to drive the vehicle to advance, the vehicle inspection system further comprises a driving passage arranged in the inspection passage and used for enabling the vehicle to voluntarily pass, and the driving passage is arranged to be substantially parallel to the dragging means, and under the first mode, the vehicle voluntarily passes the inspection passage.

According to one aspect of the present invention, the vehicle inspection system is integrated with a highway charging card interface.

According to one aspect of the present invention, the elongated traction element is a chain or a plate link chain.

The vehicle inspection system according to the embodiments of the present invention can be used for easing or eliminating the influence of the dragging equipment on the scanned image.

BRIEF DESCRIPTION OF THE DRAWINGS

FIG. 20 is a schematic diagram of a structure of a plate link chain of a dragging means of a vehicle dragging system of a vehicle inspection system according to an embodiment of the present invention, wherein (A) is a front view and (B) is a top view;

DETAILED DESCRIPTION OF THE EMBODIMENTS

Embodiment 1

Figure 1:
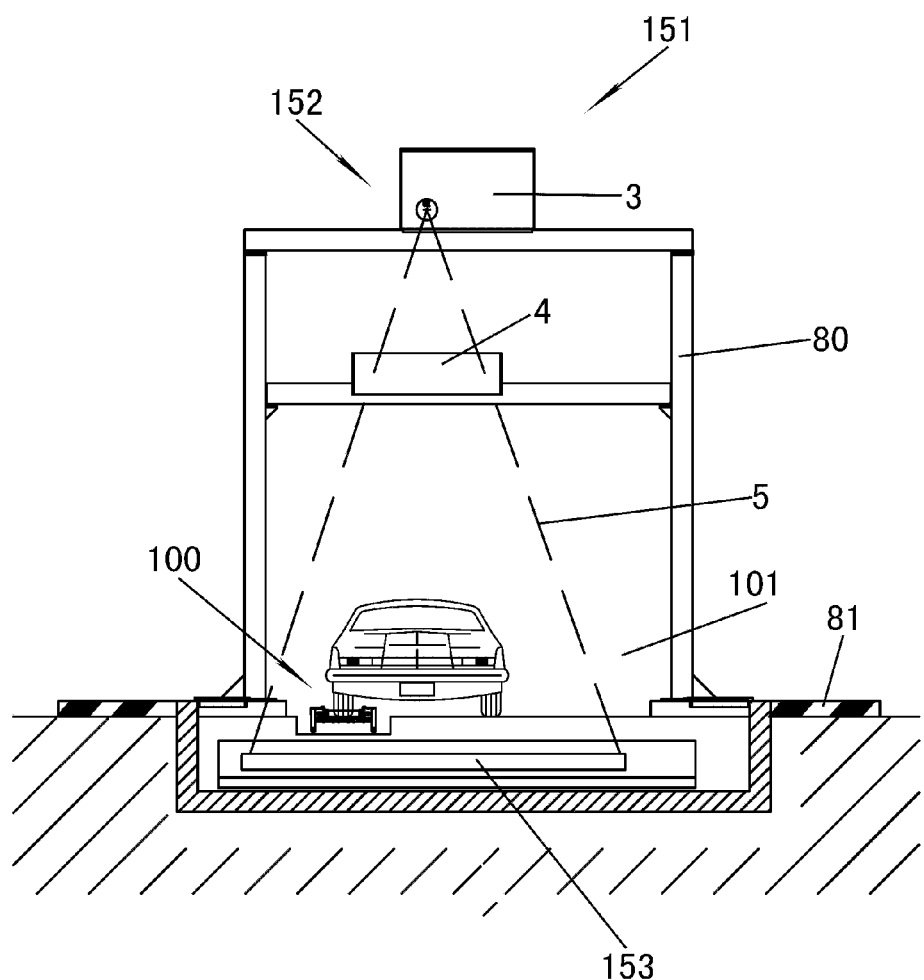
FIG. 1 is a front view of an embodiment of an inspection system according to an embodiment of the present invention.

As shown in FIG. 1, a vehicle inspection system according to an embodiment of the present invention includes: an inspection passage 101, a vehicle dragging system 100 and a radiographic inspection system 151.

Figure 2:
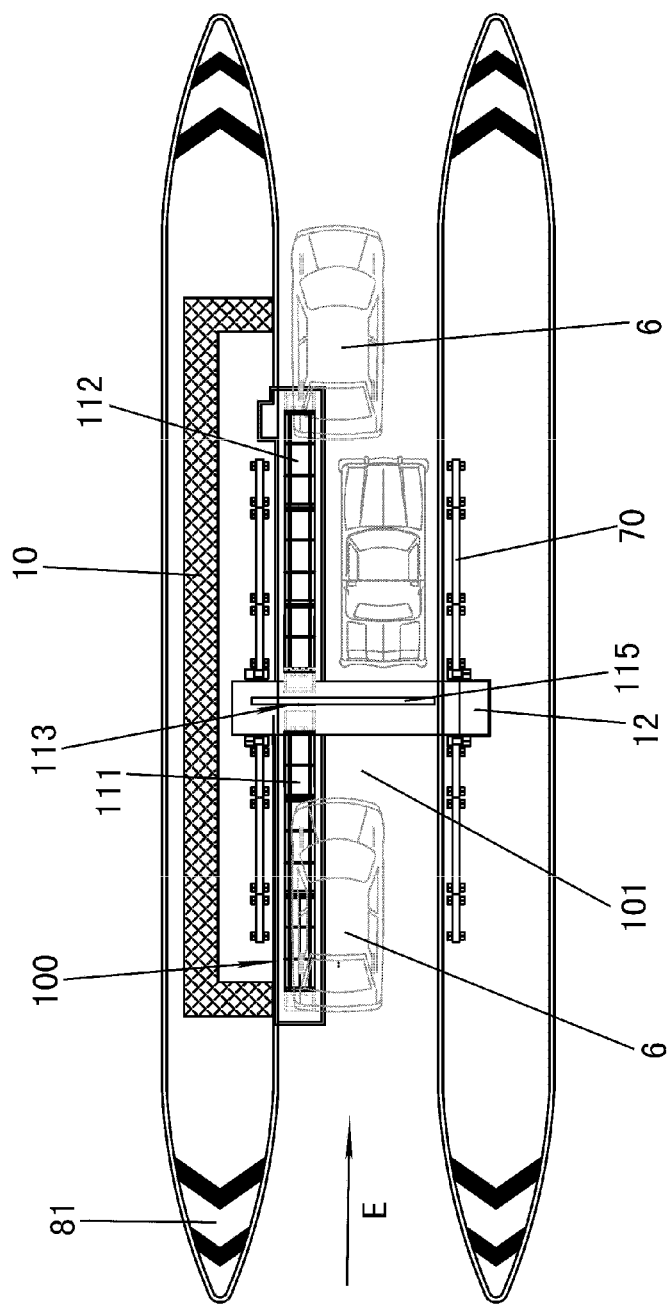
FIG. 2 is a top view of an embodiment of an inspection system according to the present invention.

As shown in FIG. 2, the vehicle dragging system 100 includes a first dragging means 111 and a second dragging means 112, which are sequentially arranged along a vehicle dragging direction E, wherein in the vehicle dragging direction E, the first dragging means 111 is arranged at the upstream of the second dragging means 112, and a separating section 113 is arranged between the first dragging means 111 and the second dragging means 112, for separating the first dragging means 111 from the second dragging means 112 at a preset distance in the vehicle dragging direction E. The first dragging means 111 and the second dragging means 112 are arranged in the inspection passage 101. At least a part of the paths of the beams of the radiographic inspection system 151 penetrates through the separating section 113 between the first dragging means 111 and the second dragging means 112.

In some embodiments of the present invention, as shown in FIG. 1 and FIG. 2, the radiographic inspection system 151 includes a radiation source 152 arranged at one of the upper side and the lower side of the separating section 113 between the first dragging means 111 and the second dragging means 112, and a detector 153 at least partially arranged at the other one of the upper side and the lower side of the separating section 113 between the first dragging means 111 and the second dragging means 112 and used for receiving beams emitted by the radiation source 152 and penetrating through the inspected vehicle. The radiation source 152 can be an X radiation source or other suitable radiation sources.

For example, as shown in FIG. 1 and FIG. 2, radiation shield walls 70 are arranged at the two sides of the inspection passage 101, a scanning means framework 80 is arranged within the range of the inspection passage 101, the radiation source 152 is arranged at the top of the scanning means framework 80 for scanning the vehicle passing the inspection passage 101, and the detector 153 is arranged under the ground corresponding to the radiation source 152.

Figure 11:
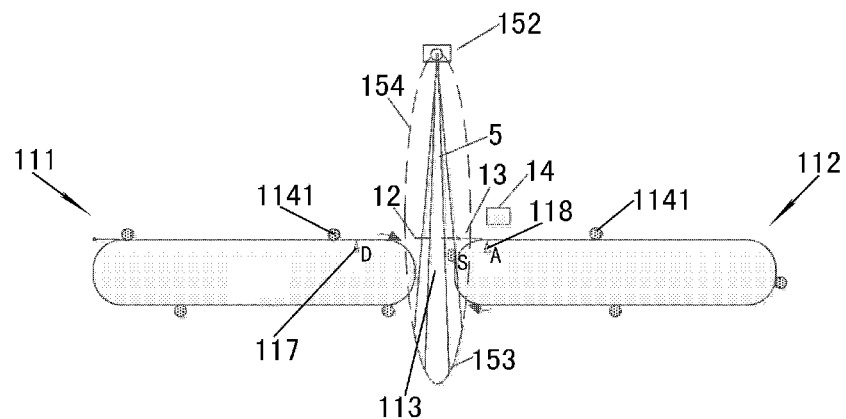
FIG. 11 is a schematic diagram of a vehicle inspection system adopting a CT system according to another embodiment of the present invention, wherein a vehicle dragging system includes two dragging means.

In some embodiments of the present invention, as shown in FIG. 11, the radiographic inspection system 151 may include a slip ring 154, a radiation source 152 installed on the slip 154, and a detector 153 installed on the slip ring 154, wherein the detector 153 is used for receiving the beams emitted by the radiation source 152 and penetrating through the inspected vehicle. The slip ring 154 is driven by a driving mechanism to rotate, in order to drive the radiation source 152 and the detector 153 to rotate around the vehicle.

As shown in FIG. 14, FIG. 15, FIG. 20, FIG. 21 and FIG. 22, the first dragging means 111 includes a first supporting plate 1111, a first chain 114 (an example of an elongated traction element) and a first pushing element 1141 connected with the first chain 114, and the first pushing element 1141 moves around the first supporting plate 1111 for pushing wheels to move along the first supporting plate 1111, in order to drive a vehicle to advance. The second dragging means 112 includes a second supporting plate 1121, a second chain 114 (an example of the elongated traction element) and a second pushing element 1141 connected with the second chain 114, and the second pushing element 1141 moves around the second supporting plate 1121 for pushing the wheels to move along the second supporting plate 1121, in order to drive the vehicle to advance.

See FIG. 3, FIG. 7, FIG. 8, FIG. 9, FIG. 10 and FIG. 11, the vehicle dragging system further includes a controller (not shown), wherein the controller controls the first pushing element 1141 to push a first wheel of the vehicle at a first speed, when a second wheel of the vehicle arrives at a preset position A of the second dragging means 112 away from the separating section 113 at a preset distance, the second chain 114 moves, thus the second pushing element 1141 at the lower side of the second supporting plate 1121 moves to contact the second wheel of the vehicle at a second speed and push the second wheel of the vehicle, in order to keep the moving state of the vehicle, and in the vehicle dragging direction E, the second wheel is located at the downstream side of the first wheel. The second speed may be larger than or equal to the first speed, and the second speed and the first speed may be basically constant. Before the first pushing element 1141 is separated from the first wheel, the second pushing element 1141 contacts the second wheel.

Figure 3:
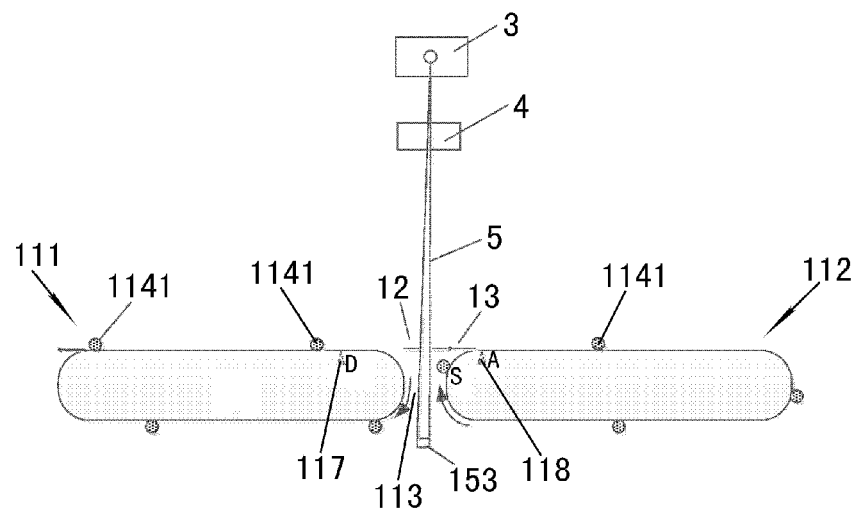
FIG. 3 is a schematic diagram of a vehicle inspection system according to an embodiment of the present invention, wherein a vehicle dragging system includes two dragging means.

As shown in FIG. 3, the vehicle dragging system further includes a sensor 118 used for sending a signal when the second wheel of the vehicle arrives at the preset position A, and the sensor 118 is located at the preset position A of the second dragging means 112 away from the separating section 113 for the preset distance. After receiving the signal of the sensor 118, the controller allows the second chain 114 to perform accelerated motion, and allows the second pushing element 1141 located at the lower side of the second supporting plate 1121 to move for a preset time, touch the second wheel of the vehicle at the second speed and push the second wheel of the vehicle. The sensor 118 can be a pressure sensor, a photoelectric sensor or a piezoelectric sensor or the like, and the pressure sensor, the photoelectric sensor or the piezoelectric sensor or the like is arranged at the preset position A of the second dragging means 112.

For example, as shown in FIG. 3, the vehicle moves from left to right, the pushing element 1141 of the first dragging means 111 pushes the rear wheel of the vehicle, in order to allow the vehicle to move rightwards at a first speed V. When the front wheel of the vehicle arrives at the sensor 117 arranged at the preset position D, the pushing element 1141 on the second dragging means 112 stops at an S point.

According to an embodiment of the present invention, when the front wheel of the vehicle arrives at the preset position A, after receiving the signal of the sensor 118, the controller allows the second chain 114 to perform accelerated motion and then decelerate to the second speed. The accelerated motion can be uniformly accelerated motion, and the decelerated motion can be uniformly decelerated motion (匀减速). The pushing element 1141 of the second dragging means 112 performs accelerated motion and accelerates to a speed V2 (V2>V), keeps the speed V2 and then pushes the front wheel of the vehicle to move. Preferably, when the moving speed of the vehicle becomes the speed V2, the beam emission frequency of an X-ray beams generating means 3 (or the stretch factor of a local image) is changed. For example, the ratio of the vehicle speed to the beam emission frequency is constant. Preferably, the system adopts a speed measuring means to track the speed of the vehicle when moving from the first dragging means 111 to the second dragging means 112 and is driven on the second dragging means 112, and when the vehicle speed changes, the beam emission frequency of the X-ray beams generating means 3 is changed. The accelerated motion of the pushing element 1141 can be uniformly accelerated motion.

In the embodiment as shown in FIG. 1, the radiation source 152 includes the X-ray beams generating means 3 and a beam collimator 4, and the beam emission range of beams is shown by a dotted line as shown by reference sign 5. According to a preferable embodiment of the present invention, the beam generating means includes an electronic linear accelerator (e.g., a 1.5 MeV electronic linear accelerator) or an X-ray beams machine. Preferably, the width of the inspection passage 101 is 3.5 m and the height thereof is 4 m. Correspondingly, the width of the top of the vehicle capable of being inspected by the vehicle inspection system disclosed by the present invention is not larger than 1.8 m, the width of the bottom of the vehicle is not larger than 2.4 m and the height is not larger than 2 m. Preferably, as shown in FIG. 1, the X-ray beams generating means 3 is arranged at the top of the scanning means framework 80, and the beam collimator 4 is arranged at the lower side. When the vehicle drives into the inspection passage 101 and enters the main beam range 5 of the beams, the vehicle is scanned by X-ray beams, and the detector 153 arranged underground receives the X-ray beams. Preferably, the detector 153 adopted herein is a 5 mm×2.5 mm cadmium tungstate array detector, which acquires an overlooking image of the vehicle through vertical transmission imaging technology. Preferably, the scanning speed is 0.1 m/s or 0.2 m/s.

The inspected vehicle can be a small vehicle, for example, the vehicle can be a passenger car or a coach.

The above-mentioned specific arrangement parameters and selected means are merely used for exemplarily illustrating the solutions of the present invention, rather than limiting the technical solutions of the present invention, those skilled in the art can select other parameters and means according to actual demands, and these variations or medications are all within the protection scope of the present invention.

As shown in FIG. 1, the vehicle inspection system disclosed by the present invention can be integrated with a highway toll station to perform security inspection work of important transportation hubs, reference sign 81 expresses safety islands at the two sides of the inspection passage, and the safety islands 81 can be seen more clearly in FIG. 2. The vehicle inspection system disclosed by the present invention can also be applied to places in fields such as important buildings, important activity areas or land border ports or the like, to perform security inspection work.

According to the preferable embodiment of the present invention, the first dragging means 111 and the second dragging means 112 are arranged at one side in the inspection passage 101 and can drag the vehicle driving into the inspection passage 101 to pass the inspection passage 101. The first dragging means 111 pushes the rear wheels of the vehicle, and then the second dragging means 112 pushes the front wheels of the vehicle, thus the separating section 113 is arranged between the first dragging means 111 and the second dragging means 112. The path of the beams from the radiation source 152 to the detector 153 passes the separating section 113, in order to avoid the influence of the first dragging means 111 and the second dragging means 112 on a scanned image.

According to some embodiments of the present invention, the width of the inspection passage 101 is arranged in such a manner that the vehicle can pass the inspection passage 101 through the vehicle dragging system 100, and meanwhile, the vehicle can pass the inspection passage 101 along the ground with no dragging means.

Specifically, see FIG. 2, the direction E is the vehicle travelling direction. According to the preferable embodiment of the present invention, the condition that the vehicle in dotted lines is dragged to the exit of the inspection passage 101 by the vehicle dragging system 100, security inspection is performed on the vehicle, under the condition, an unmanned mode is adopted, a driver leaves the vehicle at the starting point where the vehicle 6 enters the first dragging means 111, and walks to the destination of the second dragging means 112 through a passage 10 to wait for the vehicle after inspection. The passage 10 is arranged at the rear side of the radiation shield walls 70, in order to prevent the driver of suffering from radiation of the X-ray beams. FIG. 2 also shows another condition, namely, the vehicle is not dragged by the vehicle dragging system 100, but the driver quickly drives over the inspection passage 101, and the inspection system can select to scan the vehicle by adopting a radiation dosage safe for the driver, or select to not scan the vehicle. In other words, according to the technical solutions provided by the present invention, the vehicle passes the inspection passage 101 in one of the above-mentioned three manners. Namely, different vehicles can be classified, the vehicles needing no security inspection can pass without being dragged by the vehicle dragging system 100, and are driven to quickly pass the inspection passage 101; the vehicles with low security risk may be not dragged by the vehicle dragging system 100 and are scanned at a low radiation dosage when quickly passing the inspection passage 101; the vehicles with high security risk are dragged by the vehicle dragging system 100 to pass the inspection passage 101 for scanning at a standard radiation dosage, in this way, the security inspection working efficiency can be greatly improved and traffic jams are improved.

Preferably, a single dragging means herein can be a dragging means in the car washer industry, namely, a single side wheel dragging means, since the dragging means has been commonly applied in the car washing industry, it can be introduced into the vehicle security inspection field as mature technology, such that repeated research and development on a vehicle moving means are avoided. The dragging means is most labor-saving, energy-saving and environmental-friendly; a truckle only contacts the wheels, thus generating the minimum wear and collision on vehicles, as a result, it is easy to be accepted by owners and drivers.

Besides the above-mentioned advantages, the vehicle inspection system provided by the present invention can be directly built on the safety island of an existing toll station, thus the civil engineering workload is small and the floor space is small. Furthermore, being similar to a small luggage X-ray beams security inspection machine, when the vehicle passes an X ray beam flow surface, a scanned image is automatically acquired in real time, thus the security inspection efficiency and accuracy are greatly improved.

FIG. 3 shows a schematic diagram of a vehicle inspection system including the first dragging means 111 and the second dragging means 112. The separating section 113 is arranged between the first dragging means 111 and the second dragging means 112, and beams 5 penetrate through the separating section to irradiate the detector 153.

Preferably, as shown in FIG. 2 and FIG. 3, the separating section 113 between the first dragging means 111 and the second dragging means 112 is provided with a platform 12, which is convenient for the vehicle to travel on the separating section 113 between the first dragging means 111 and the second dragging means 112. The upper surface of the platform 12 and the ground plane in the inspection passage are in the same height. A gap 115 can be formed at the middle of the platform 12, in order to prevent the beams from the collimator 4 to the detector 153 from being shielded to truly realize non-shielded scanning of the entire dragging means. The gap 115 may be formed in the separating section 113.

Alternatively, one material with the same thicknesses as that of the gap can be arranged in the gap 115 of the platform 12 to improve the sealing property of the system. This nearly generates no influence on the scanned image, because the one material with the thickness would add uniform backgrounds on the image. Of course, the materials are selected by comprehensively considering beam penetrability loss, physical strength and price of materials, for example, aluminum, iron, plastic and carbon fiber and other materials.

As shown in FIG. 3, an overturning plate 13 facilitates passage of vehicle wheels and allows the pushing element 1141 on the second dragging means 112 to pass, and the overturning plate 13 can rotate around a pivot. The pivot is perpendicular to the extension direction of the second dragging means 112 or the direction E.

Embodiment 2

A scanned vehicle passes a scanning area at a constant speed, which will bring great inconvenience to scanning control and data processing, and the purpose of the embodiment is to enable the vehicle to pass the separating section 113 between the first dragging means 111 and the second dragging means 112 at the constant speed.

Figure 4:
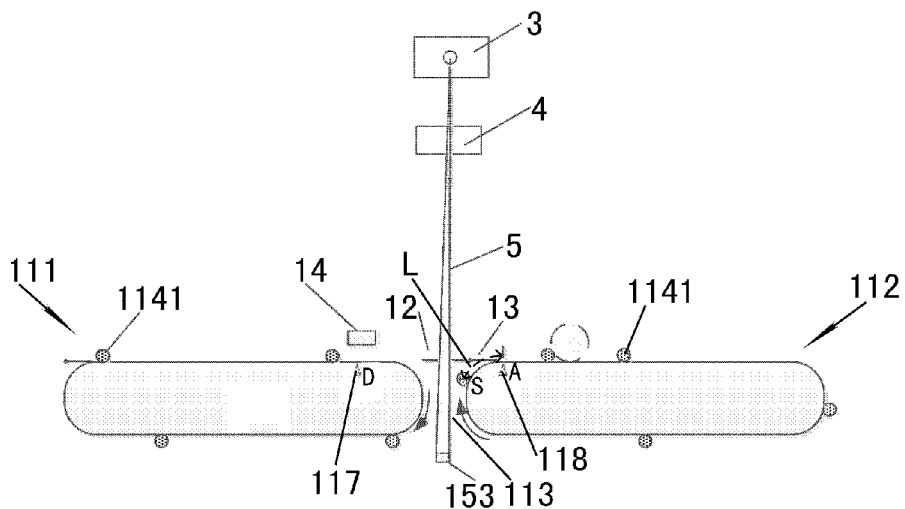
FIG. 4 is a schematic diagram of a vehicle inspection system according to another embodiment of the present invention, wherein a vehicle dragging system includes two dragging means.

The structure of the system in the embodiment is as shown in FIG. 1 and FIG. 2 as well, and the dragging means is as shown in FIG. 4. The main difference between FIG. 4 and FIG. 3 lies in that an image acquiring means 14 is arranged at one side (adjacent to the first dragging means 111) of the inspection passage 101 and is located near the preset position D.

As shown in FIG. 4, the vehicle dragging system further includes a sensor 118 used for sending a signal when the second wheel of the vehicle arrives at the preset position A, and the sensor 118 is located at the preset position A of the second dragging means 112 away from the separating section 113 for the preset distance. After receiving the signal from the sensor 118, the controller allows the second chain 114 to perform accelerated motion, and allows the second pushing element 1141 located at the lower side of the second supporting plate 1121 to move for a preset time, contact the second wheel of the vehicle at the second speed and push the second wheel of the vehicle. The sensor 118 can be a pressure sensor, a photoelectric sensor or a piezoelectric sensor or the like, and the pressure sensor, the photoelectric sensor or the piezoelectric sensor or the like is arranged at the preset position A of the second dragging means 112.

As shown in FIG. 4, the vehicle dragging system further includes a wheel diameter acquiring means used for measuring the diameter of the second wheel of the vehicle, and a calculating means, wherein the calculating means is used for calculating a travelling distance necessary for the second pushing element 1141 to catch up with the second wheel and contact the second wheel, according to the diameter of the second wheel acquired by the vehicle diameter acquiring means and the position of the second pushing element 1141 located at the lower side of the second supporting plate 1121. The wheel diameter acquiring means can include an image acquiring means, and the image acquiring means is used for acquiring two images including the second wheel at a preset time interval, and calculating the diameter of the second wheel of the vehicle according to the vehicle displacement distances in the two images, the first speed of the vehicle, the diameters of the second wheel of the vehicle in the images and the time interval. The image acquiring means can be a camera or video camera 14, is arranged at the preset position D of the first dragging means 111 away from the separating section 113 by a preset distance and is located at one side of the first dragging means 111.

For example, as shown in FIG. 4, the vehicle moves from left to right, the pushing element 1141 of the first dragging means 111 pushes the rear wheel of the vehicle, in order to allow the vehicle to move rightwards at the first speed V. When the front wheel of the vehicle arrives at the sensor 117 arranged at the preset position D (ground), the pushing element 1141 on the second dragging means 112 stops at the S point, and the camera or video camera 14 is started to shoot the vehicle. After a short time interval t, the vehicle is shot again. The camera or video camera 14 can clearly shoot the front wheel of the vehicle and the nearby area thereof.

Figure 5:
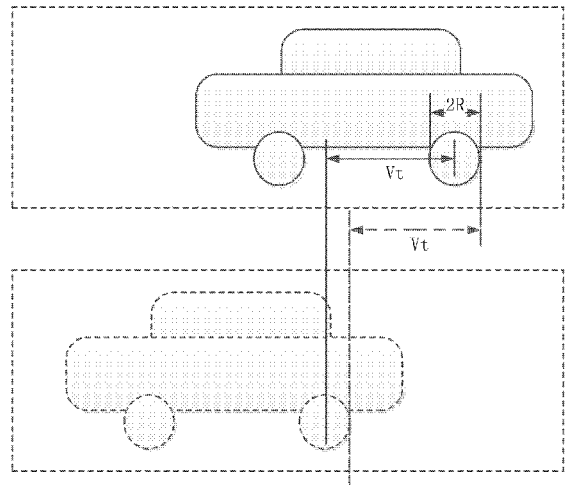
FIG. 5 is a schematic diagram of measurement by twice photographing.

As shown in FIG. 5, the camera or video camera 14 shoots a photograph of the inspected vehicle and shoots a photograph again at a time interval t. The vehicle moves at the speed V, and the vehicle advances a distance Vt within the time t. The outside diameter of the front wheel of the vehicle is measured on the photograph, and the vehicle moving distances are measured on two photographs, in this way, two measurements can be manually performed on the photographs, and can also be automatically processed by use of an image processing algorithm. The outside diameter of the front wheel of the vehicle:

$$2R = Vt \times \frac{\text{outside diameter of front wheel of vehicle on the photograph}}{\text{staggered distance of vehicle on two photographs}} \quad (1)$$

In this way, the outside diameter of the front wheel of the vehicle can be measured, and the measurement of the outside diameter of the front wheel is very important for the second pushing element 1141 on the second dragging means 112 to contact the wheel of the vehicle at a preset speed. Of course, under the condition that the outside diameter of the front wheel is known, the travelling speed can be measured in return. Alternatively, under the condition that the outside diameter of the front wheel and the travelling speed are known, the time interval is measured by the technology. The method is liable to expand to various fields, such as size measurement, speed measurement, time measurement and the like, and the measurement object is not limited to vehicles or wheels. In addition, the purpose of improving the precision can be realized by improving the measurement precision of each parameter, selecting multiple data measurement points or shooting for multiple times.

Of course, vehicle type identification or other methods for measuring the diameter of the front wheel can replace the above-mentioned shooting measurement method to complete the step of measuring the diameter of the front wheel in the present invention. However, the shooting measurement method has the advantages of low cost, mature equipment technology, saving occupation area and the like.

Figure 6:
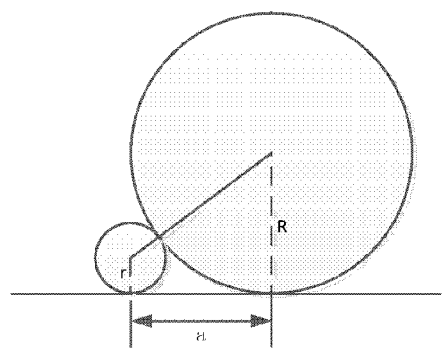
FIG. 6 is a position diagram when a pushing element, e.g., a roller contacts a wheel.

As shown in FIG. 6, under the condition that the pushing element 1141 is a roller, after the diameter of the front wheel is measured, when the pushing element 1141 of the second dragging means 112 pushes the front wheel, the relative distance a therebetween can be accurately calculated. If the diameter 2R of the front wheel and the radius r of the pushing element 1141 are known, it can be obtained that $$a = \sqrt{(R+r)^2 - (R-r)^2} = 2\sqrt{Rr} \quad (2)$$

Figure 7:
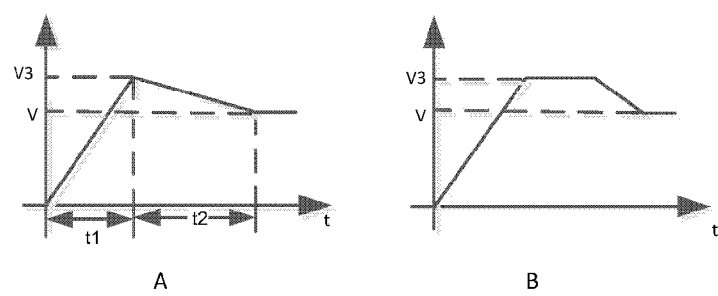
FIG. 7 is a speed-time curve of a pushing element, e.g., a roller.

For example, when the front wheel of the vehicle arrives at the sensor 118 at the preset position A, the pushing element 1141 of the second dragging means 112 performs accelerated motion and accelerates to a speed V3 (V3>V), gradually decelerates to the speed V and then pushes the front wheel of the vehicle to move. The motion rate-time relationship of the pushing element 1141 of the second dragging means 112 is preferably as shown in FIG. 7 (A). The pushing element 1141 accelerates to the speed V3 from a static state after a time t1 and then decelerates to V after a time t2. As shown in FIG. 4, the distance from the S to the position A is L. The pushing element 1141 chases the front wheel and needs to travel a distance L-a more than the vehicle. The pushing element 1141 moves according to the rate-time curve as shown in FIG. 7, $$L-a = 0.5 \times [V3 \times t1 + (V3+V) \times t2] - V \times (t1+t2) \quad (3)$$

V3, t1 and t2 can be flexibly designed according to demand, but before the rear wheel arrives at the platform 12 as shown in FIG. 4, the pushing element 1141 must catch up with the front wheel at the speed V. By the way, the measurement of L can be calculated by the accurate size of the second dragging means 112 and can also be deduced according to the time interval of the pushing element 1141 for passing through the position S and the position A at a constant speed, and can be used as a parameter of the system.

Preferably, the accelerated motion and decelerated motion of the pushing element 1141 are uniformly accelerated motion and uniformly decelerated motion.

Obviously, the pushing element 1141 can chase the front wheel according to other rate-time curves, for example, according to FIG. 7 (B). When the front wheel of the vehicle arrives at the preset position A, the pushing element 1141 accelerates to the speed V3, constantly advances at the speed V3 and then decelerates to V and catches up with the front wheel of the vehicle. According to the forgoing manner, a kinematic formula can be obtained, and will not be repeated herein. Actually, according to the properties of a motor and by adopting a specific rate-time curve, various chasing manners can be designed, including variable acceleration chasing, as long as the chasing distance L-a is obtained.

In the solution of the embodiment, the moving speed of the vehicle is kept to V, and the beam emission frequency of the X-ray beams generating means 3 is not necessarily changed, so that the beam emission and detection system control complexity is reduced.

Embodiment 3

In the embodiment 2, it is realized that the vehicle passes the separating section 113 at the constant speed and the dragging means does not shield the scanning beams. The method for measuring the outside diameter of the wheel is also provided. But the system is slightly complicated, including that the distance L as shown in FIG. 4 needs to be measured. In the embodiment 3, based on the measurement of the outside diameter of the wheel, the vehicle is kept to move at the constant speed, and the L value does not need to be measured.

Figure 8:
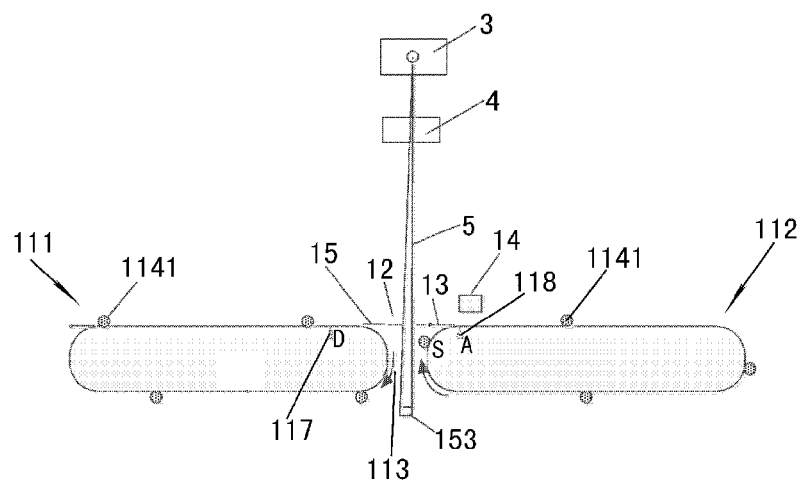
FIG. 8 is a schematic diagram of a vehicle inspection system according to another embodiment of the present invention, wherein a vehicle dragging system includes two dragging means.
Figure 9:
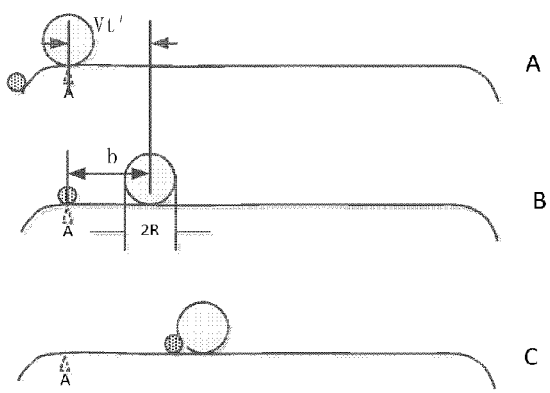
FIG. 9 is a schematic diagram of controlling a pushing element according to another embodiment of the present invention.
Figure 10:
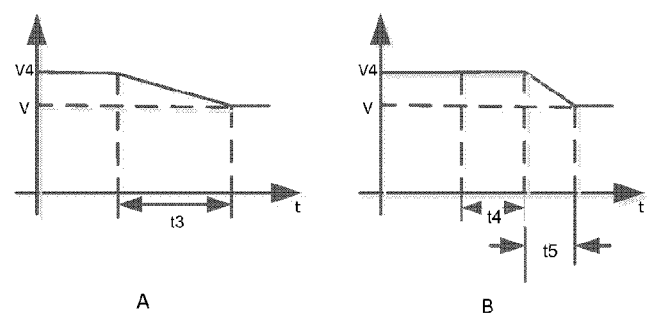
FIG. 10 is a schematic diagram of a speed-time curve of a pushing element, e.g., a roller.

Compared with the embodiment 2, the major modification in system deployment is as follows: the image acquiring means 14 is changed from the preset position D to a position near the preset position A and is adjacent to one side of the dragging means, as shown in FIG. 8.

As shown in FIG. 8, the vehicle dragging system further includes a distance acquiring apparatus used for measuring the distance between the second wheel of the vehicle and the second pushing element 1141, when the second wheel of the vehicle arrives at the preset position A of the second dragging means 112 away from the separating section 113 for the preset distance, the distance acquiring apparatus acquires the distance between the second wheel and the second pushing element 1141 to serve as the travelling distance necessary for the second pushing element 1141 to catch up with the second wheel and contact the second wheel.

See FIG. 8, the distance acquiring apparatus may include an image acquiring means, wherein the image acquiring means 14 is used for acquiring two images including the second wheel and the second pushing element 1141 at a preset time interval, and calculating the distance between the second wheel and the second pushing element 1141 according to the vehicle displacement distances in the two images, the distance between the second wheel and the second pushing element 1141, the first speed of the vehicle and the time interval. The image acquiring means may be a camera or video camera, can be arranged at the preset position A of the second dragging means 112 away from the separating section 113 for the preset distance and is located at one side of the second dragging means 112.

In this way, the image acquiring means can be not only used for acquiring the diameter of the second wheel of the vehicle, but also used for acquiring the distance between the second wheel and the second pushing element 1141, and the distance is the foundation for calculating the travelling distance necessary for the second pushing element 1141 to catch up with the second wheel and contact the second wheel. It is not difficult to understand that an accurate chasing distance should be acquired by subtracting the distance in the vehicle traveling direction of the second wheel and the second pushing element when the second wheel contacts the second pushing element from the distance (for such circular pushing elements as a pushing roller, it is a in the formula 2).

As shown in FIG. 8, the vehicle dragging system further includes a sensor 118 used for sending a signal when the second wheel of the vehicle arrives at the preset position A away from the separating section 113 for the preset distance of the second dragging means 112, after receiving the signal of the sensor 118, the controller operates the distance acquiring apparatus to acquire the distance between the second wheel and the second pushing element 1141. The sensor 118 can be a pressure sensor, a photoelectric sensor or a piezoelectric sensor or the like, and the pressure sensor, the photoelectric sensor or the piezoelectric sensor or the like is arranged at the preset position A of the second dragging means 112.

Preferably, as shown in FIG. 8, the vehicle moves from left to right, the pushing element 1141 of the first dragging means 111 pushes the rear wheel of the vehicle, in order to allow the vehicle to move rightwards at the first speed V. When the front wheel of the vehicle arrives at the first sensor 117 arranged at the preset position D, the pushing element 1141 on the second dragging means 112 stops at the S point and begins to start to a speed V4 (V4>V). When the front wheel of the vehicle arrives at the second sensor 118 (the photoelectric sensor or the piezoelectric sensor) at the second preset position A, the vehicle and the front wheel thereof are shot, as shown in FIG. 9A. When the pushing element 1141 on the second dragging means 112 arrives at the second sensor 118 at the preset position A, the vehicle and the front wheel thereof are shot again, as shown in FIG. 9B. A system timer (not shown) records the time interval t' of twice shooting. Similar to the foregoing principle of measuring the outside diameter 2R of the front wheel, it is easy to acquire:

$$2R = Vt' \times \frac{\text{outside diameter of front wheel of vehicle on photographs}}{\text{staggered distance of vehicle on two photographs}} \quad (4)$$

during the second time shooting, the distance between the pushing element 1141 and the front wheel of the vehicle is measured on the photograph as well. Then, the actual distance b between the pushing element 1141 and the front wheel of the vehicle satisfies a formula:

$$b = Vt' \times \frac{\text{distance between front wheel of vehicle and pushing element on the photographs}}{\text{staggered distance of vehicle on two photographs}} \quad (5)$$

wherein the pushing element 1141 needs to chase for a distance b-a to catch up with the front wheel of the vehicle (a is acquired by substituting R calculated in formula 4 into the formula 2).

When the pushing element 1141 arrives at the preset position A, the pushing element 1141 begins to uniformly decelerate to the speed V after a time t3 and catches up with the front wheel of the vehicle (as shown in FIG. 9C), the speed-time curve is as shown in FIG. 10A, it can be known that:

$$b-a=0.5 \times (V4-V)t3 \quad (6)$$

the acceleration is equal to $$p=(V-V4)/t3 \quad (7)$$

Beginning from the front wheel arrives at the preset position A until the pushing element 1141 catches up with the front wheel, the moving distance of the vehicle is equal to V (t'+t3). As shown in FIG. 8, the space from the edge of the first dragging means 111 to the preset position A is g. In order to ensure that before the first pushing element 1141 of the first dragging means 111 is separated from the first wheel (e.g., the rear wheel), the second pushing element 1141 of the second dragging means 112 contacts the second wheel (e.g., the front wheel), it is assumed that the minimum value of the space between the front and rear wheels of all common vehicles is equal to M, then $$V(t'+t3)+g<M \quad (8)$$

and this condition should be satisfied in system design.

System parameters and control parameters are designed according to the formulas 6-8: the acceleration p, the speed V4, the time intervals t', t3, and intermediate calculation is completed by the formulas 4-5. Therefore, the vehicle can stably pass the separating section 113 at the constant speed.

Of course, the speed-time curve of the pushing element 1141 can be changed from FIG. 10A into FIG. 10B, namely, after arriving at the preset position A, the pushing element 1141 continues to travel a time t4 at the constant speed, then uniformly decelerates to the speed V after a time t5 and catches up with the front wheel of the vehicle. This manner facilitates accelerating the chasing progress. Additional time parameter is adjustable, thus increasing the design flexibility of the system. Of course, the solution is a little more complicated to be controlled than the solution as shown in FIG. 10A. Actually, the pushing element 1141 can chase the front wheel according to various speed-time curves, including variable accelerated motion, as long as it is satisfied that the speed of the pushing element 1141 is equal to the speed of the vehicle, when the pushing element catches up with the front wheel.

In the embodiment, the positioning of the preset position D and the preset position S is not necessarily very accurate, thus the system cost can be further reduced.

As shown in FIG. 8, in order to enable the vehicle to stably pass the separating section 113 between the first dragging means 111 and the second dragging means 112, a pedal 15 can be arranged in the system. When the front wheel arrives at the preset position D, the pedal 15 is stretched out to enable the front wheel to stably pass. The pedal 15 is retracted after the front wheel passes. Of course, the pedal 15 can be omitted under the condition that the requirement on the stable travelling of the vehicle is not particularly high or the diameter of the pushing element 1141 is small enough.

Actually, by means of the speed-time curve and the technology of the present invention, the vehicle pushing speeds of the first dragging means 111 and the second dragging means 112 can be randomly controlled, so as to meet a variety of application demands.

Embodiment 4

The dragging system in the foregoing embodiments 1, 2 and 3 are applied to a perspective scanning imaging system to achieve no shielding to beams. As mentioned above, the radiographic inspection system in the present invention can include a CT scanning system, as shown in FIG. 11. The radiation source 152 and the detector 153 are installed on the slip ring 154. The dragging system in the present invention can also be applied to a nuclear magnetic resonance imaging system, to avoid the influence of the dragging means on imaging.

Figure 12:
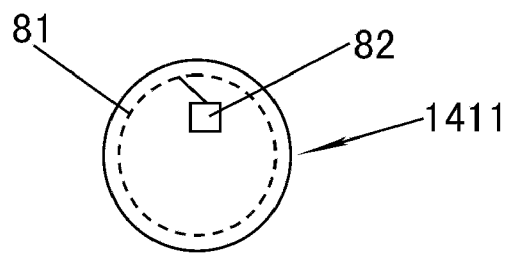
FIG. 12 is a schematic diagram of a pushing element of a vehicle inspection system according to an embodiment of the present invention, wherein the pushing element is provided with a detecting means used for detecting whether the pushing element contacts a wheel of a vehicle and a feedback means.

As shown in FIG. 12, the vehicle dragging system further includes a sensor 81, wherein the sensor 81 is arranged on the second pushing element 1141 and is used for detecting whether the second pushing element 1141 has been in contact with the second wheel (e.g., the front wheel) of the vehicle. The sensor can be a contact sensor, a pressure sensor, a piezoelectric sensor or the like. The vehicle dragging system further includes a feedback means 82. The sensor detects whether the second pushing element 1141 has been in contact with the front wheel and notifies the controller of the vehicle inspection system through the connected feedback means 82. After receiving the signal that the second pushing element 1141 has been in contact with the second wheel (e.g., the front wheel) of the vehicle, the controller of the vehicle inspection system can control the second dragging means 112 to push the vehicle to advance at a pushing speed larger than that of the first dragging means 111. As another alternative preferable solution, after receiving the signal that the second pushing element 1141 has been in contact with the second wheel (e.g., the front wheel) of the vehicle, the vehicle inspection system can control the second dragging means 112 to push the vehicle to advance at a pushing speed equal to the pushing speed of the first dragging means 111, namely, dragging the vehicle at a constant speed. Apparently, in the solution, the image acquiring means 14 as shown in FIG. 8 can be omitted, and even the sensor 117 at the preset position D and the sensor 118 at the preset position A as shown in FIG. 8 are omitted.

Preferably, the sensor 81 is a piezoelectric sensor. Preferably, the feedback means includes a radio signal emitting unit used for sending the signal to the controller of the vehicle inspection system.

According to the vehicle inspection system provided by the present invention, the vehicle inspection system can be integrated with a highway toll station to perform online quick security inspection on vehicles; the radiation shield walls are arranged to avoid accidental radiation on pedestrians or drivers; the dragging means can be used for dragging the vehicles to pass the inspection passage 101 under an unmanned condition, and small vehicles can voluntarily and quickly pass the inspection passage 101 without using the dragging means, such that different vehicles can be processed in a classification manner, which is beneficial to easing traffic jam.

In this way, the scanned image can be acquired by the beams in a non-shielding manner when the vehicle is dragged or driven to pass the inspection passage.

Embodiment 5

As shown in FIG. 1, the vehicle inspection system according to the embodiment of the present invention includes an inspection passage 101 for enabling a vehicle to pass, a vehicle dragging system 100 arranged in the inspection passage 101 and a radiographic inspection system 151 used for inspecting the vehicle.

As shown in FIG. 1 and FIG. 2, the radiographic inspection system 151 includes a radiation source 152 used for emitting beams, for example, providing X-ray beams for scanning the vehicle; and a detector 153 used for receiving the beams emitted by the radiation source and penetrating through the inspected vehicle, for example, used for receiving the X-ray beams emitted by the radiation source 152. Radiation shield walls 70 are arranged at the two sides of the inspection passage 101, a scanning means framework 80 is arranged within the range of the inspection passage 101, and the radiation source 152 is arranged above the inspection passage 101. For example, the radiation source 152 is arranged at the top of the scanning means framework 80, in order to scan the vehicle passing the inspection passage 101, and the detector 153 is arranged at a position opposite to the radiation source 152.

The vehicle dragging system 100 includes dragging means 111, 112, and the dragging means 111, 112 are arranged on the ground at one side within the range of the inspection passage 101 and can drag the vehicle driving into the inspection passage 101 to pass the inspection passage 101.

It should be noted that, in the embodiment, the vehicle dragging system 100 may include one or two dragging means.

The width of the inspection passage 101 is arranged in such a manner that the vehicle can pass the inspection passage 101 through the dragging means, and meanwhile, the vehicle can pass the inspection passage 101 along the ground provided with no dragging means. Namely, a travelling passage for enabling the vehicle to voluntarily pass is arranged in the inspection passage 101, and the travelling passage is arranged to be substantially parallel to the dragging means.

The vehicle inspection system further includes a pedestrian passage, wherein the pedestrian passage is arranged at the rear of the radiation shield walls 70, for allowing a driver to walk from a starting point where the vehicle is driven into the inspection passage 101 to the destination where the vehicle is about to leave the inspection passage 101.

See FIG. 14, FIG. 20, FIG. 21 and FIG. 22, each of the dragging means 111, 112 includes a chain 114 and a pushing element 1141 connected with the chain 114, and the pushing element 1141 is used for pushing wheels to move, in order to drive the vehicle to advance. The pushing element 1141 of the dragging means can merely push the left wheels or the right wheels of the vehicle.

According to some embodiments of the present invention, the first supporting plate 1111 and second supporting plate 1121 are separated at the separating section 113 and are two pieces type, and no supporting plate is provided on the separating section 113. The first and second chains 114 are continuous and integrated. Chains 114 and pushing member 1141 continuously extend on the first dragging means 111, the separating section 113 and the second dragging means 112. The vehicle inspection system further includes a controller, wherein the controller corrects an acquired image of the inspected vehicle according to a scanned image acquired by the vehicle inspection system during no load of the dragging means, in order to remove the image of the dragging means from the acquired image of the inspected vehicle, for example, the controller corrects the acquired image of the inspected vehicle according to the scanned image acquired by the vehicle inspection system during no load of the dragging means, in order to remove the image of at least one of the chain and the pushing element from the acquired image of the inspected vehicle. The controller can correct the acquired image of the inspected vehicle according to the position relationship of the inspected vehicle and at least one of the chain and the pushing element along the vehicle travelling direction, in order to remove the image of at least one of the chain and the pushing element from the acquired image of the inspected vehicle.

According to some embodiments of the present invention, the pushing element of the dragging means contacts the wheels of the vehicle and pushes the wheels, in order to determine the position relationship of the inspected vehicle and at least one of the chain and the pushing element along the vehicle travelling direction.

Figure 13:
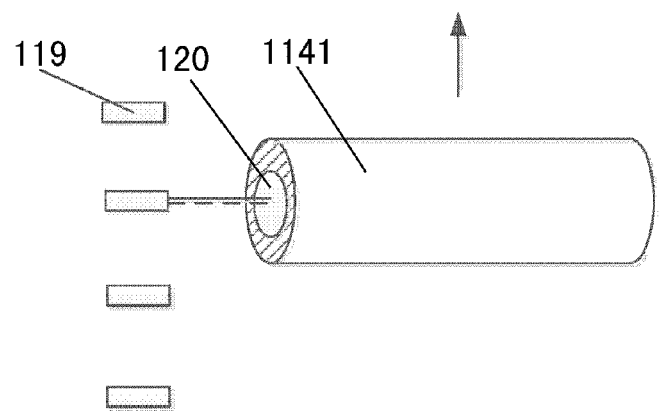
FIG. 13 is a schematic diagram of a pushing element of a vehicle inspection system according to an embodiment of the present invention, wherein a position detecting means used for detecting whether the pushing element arrives at a preset position is shown.

As shown in FIG. 13, the vehicle inspection system further includes a position detecting means 119 used for detecting whether the pushing element 1141 arrives at a preset position, and sending a signal to the controller when the pushing element pushing the wheels of the vehicle or the pushing element during no load of the dragging means arrives at the preset position, in order to start the radiographic inspection system to scan the vehicle or the no-load dragging means. The position detecting means 1141 can be an optical transceiver, the optical transceiver is arranged at one side of the dragging means and emits a light beam towards one side of the dragging means, and when the light beam irradiates a reflector 120 at the end of the pushing element 1141, the optical transceiver receives the light beam reflected by the reflector 120 at the end of the pushing element 1141, and thus determines that the pushing element 1141 arrives at the preset position.

Under the condition that the vehicle dragging system includes two dragging means, as shown in FIG. 2, the vehicle dragging system 100 includes a first dragging means 111 and a second dragging means 112, which are sequentially arranged along a vehicle dragging direction E, in the vehicle dragging direction, the first dragging means 111 is arranged at the upstream of the second dragging means 112, and a separating section 113 is arranged between the first dragging means 111 and the second dragging means 112, for enabling the first dragging means 111 and the second dragging means 112 to be separated at a preset distance in the vehicle dragging direction E. The first dragging means 111 and the second dragging means 112 are arranged in the inspection passage 101. At least a part of paths of the beams of the radiographic inspection system 151 passes through the separating section 113 between the first dragging means 111 and the second dragging means 112. As shown in FIG. 14, FIG. 15, FIG. 20, FIG. 21 and FIG. 22, the first dragging means 111 includes a first supporting plate 1111, a first chain 114 and a first pushing element 1141 connected with the first chain 114, and the first pushing element 1141 moves around the first supporting plate 1111 for pushing wheels to move along the first supporting plate 1111, in order to drive a vehicle to advance. The second dragging means 112 includes a second supporting plate 1121, a second chain 114 and a second pushing element 1141 connected with the second chain 114, and the second pushing element 1141 moves around the second supporting plate 1121 for pushing the wheels to move along the second supporting plate 1121, in order to drive the vehicle to advance.

In the vehicle inspection system according to the embodiment of the present invention, the vehicle can pass the inspection passage 101 under a first mode, a second mode or a third mode, under the first mode, the vehicle voluntarily passes the inspection passage 101, and the radiographic inspection system does not inspect the vehicle; under the second mode, the vehicle voluntarily passes the inspection passage 101, and the radiographic inspection system inspects the vehicle by adopting a dosage lower than a first preset value, wherein the dosage of the first preset value can be a maximal dosage harmless to human body and can also be a certain dosage below the maximal dosage; and under the third mode, the vehicle dragging system drags the vehicle to pass the inspection passage 101, and the radiographic inspection system inspects the vehicle by adopting a dosage larger than or equal to a second preset value, the second preset value can be the same as or different from the first preset value, and preferably, the second preset value is larger than the first preset value.

Under the first mode and the second mode, the wheels on at least one side of the vehicle drive on the first dragging means and the second dragging means, or the vehicle drives on a road beside the first dragging means and the second dragging means. As mentioned above, the vehicle inspection system further includes a travelling passage arranged in the inspection passage 101 and used for enabling the vehicle to voluntarily pass, the travelling passage is arranged to be substantially parallel to the dragging means, and under the first mode, the vehicle voluntarily drives over the travelling passage.

According to some embodiments, the vehicle can be a passenger car or a coach. The vehicle inspection system can be integrated with a highway charging card interface.

According to the embodiment of the present invention, the separating section 113 can be arranged between the first dragging means 111 and the second dragging means 112 to avoid the interference of the dragging means on the beams, or the acquired image of the inspected vehicle is corrected to remove the image of at least one of the chain and the pushing element from the acquired image of the inspected vehicle, so as to acquire an accurate image of the inspected vehicle. In addition, according to the embodiment of the present invention, the images of other (static or moving) components of the dragging means or the images of other (static or moving) components of the vehicle dragging system or the vehicle inspection system can also be removed from the acquired image of the inspected vehicle.

Embodiment 6

As shown in FIG. 1, the vehicle inspection system according to the embodiment of the present invention includes an inspection passage 101, a vehicle dragging system 100 arranged in the inspection passage and a radiographic inspection system 151.

Figure 14:
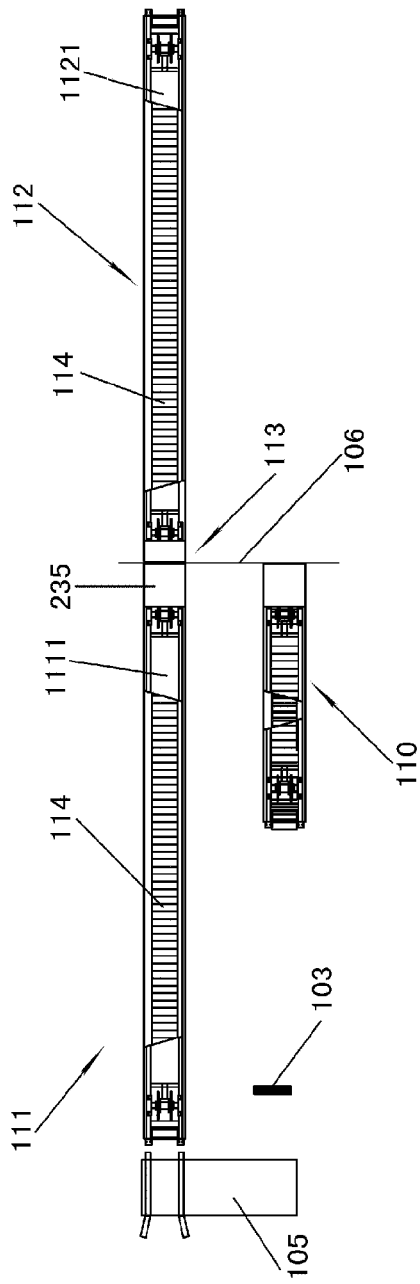
FIG. 14 is a schematic top view of a vehicle dragging system of a vehicle inspection system according to an embodiment of the present invention, wherein a dragging means of the vehicle dragging system includes a plate link chain.

As shown in FIG. 2, the vehicle dragging system 100 includes a first dragging means 111 and a second dragging means 112, which are sequentially arranged along a vehicle dragging direction E, wherein in the vehicle dragging direction, the first dragging means 111 is arranged at the upstream of the second dragging means 112, and a separating section 113 is arranged between the first dragging means 111 and the second dragging means 112, for enabling the first dragging means 111 and the second dragging means 112 to be separated at a preset distance in the vehicle dragging direction. The first dragging means 111 and the second dragging means 112 are arranged in the inspection passage 101. At least a part of paths of the beams of the radiographic inspection system 151 passes through the separating section 113 between the first dragging means 111 and the second dragging means 112. As shown in FIG. 14, a beam flow center 106 is located on the separating section 113.

In some embodiments of the present invention, as shown in FIG. 1 and FIG. 2, the radiographic inspection system 151 includes a radiation source 152 arranged at one of the upper side and the lower side of the separating section 113 between the first dragging means 111 and the second dragging means 112, and a detector 153 at least partially arranged at the other one of the upper side and the lower side of the separating section 113 between the first dragging means 111 and the second dragging means 112 and used for receiving beams emitted by the radiation source 152 and penetrating through the inspected vehicle. The radiation source 152 can be an X radiation source.

As shown in FIG. 14, FIG. 15, FIG. 20, FIG. 21 and FIG. 22, the first dragging means 111 includes a first supporting plate 1111, a first chain 114 and a first pushing element 1141 connected with the first chain 114, and the first pushing element 1141 moves around the first supporting plate 1111 for pushing wheels to move along the first supporting plate 1111, in order to drive a vehicle to advance. The second dragging means 112 includes a second supporting plate 1121, a second chain 114 and a second pushing element 1141 connected with the second chain 114, and the second pushing element 1141 moves around the second supporting plate 1121 for pushing the wheels to move along the second supporting plate 1121, in order to drive the vehicle to advance.

See FIG. 16, FIG. 17, FIG. 18 and FIG. 19, the radiographic inspection system includes:

a first radiation source 1521 arranged at one of the upper side and the lower side of the separating section 113 between the first dragging means 111 and the second dragging means 112, and a first detector 1531 at least partially arranged at the other one of the upper side and the lower side of the separating section 113 between the first dragging means 111 and the second dragging means 112 and used for receiving beams emitted by the first radiation source 1521 and penetrating through the inspected vehicle; and a second radiation source 1522 arranged at one side, in a transverse direction substantially perpendicular to an up and down direction and the vehicle dragging direction E, of the separating section 113 between the first dragging means 111 and the second dragging means 112, and a second detector 1532 at least partially arranged at the other side in the transverse direction of the separating section 113 between the first dragging means 111 and the second dragging means 112 and used for receiving beams emitted by the second radiation source 1522 and penetrating through the inspected vehicle. The first radiation source 1521 and the second radiation source 1522 are X-ray beams accelerators or X-ray beams machines, or one of the first radiation source 1521 and the second radiation source 1522 is an X-ray beams accelerator, and the other one of the first radiation source 1521 and the second radiation source 1522 is an X-ray beams machine.

Alternatively, see FIG. 16, FIG. 17, FIG. 18 and FIG. 19, the radiographic inspection system includes:

a first radiation source 1521 arranged at one of the upper side and the lower side of the separating section 113 between the first dragging means 111 and the second dragging means 112, and a first detector 1531 at least partially arranged at the other one of the upper side and the lower side of the separating section 113 between the first dragging means 111 and the second dragging means 112 and used for receiving beams emitted by the first radiation source 1521 and penetrating through the inspected vehicle, wherein the first radiation source 1521 is an X-ray beams accelerator or an X-ray beams machine, and/or the radiographic inspection system includes:

a second radiation source 1522 arranged at one side, in a transverse direction substantially perpendicular to an up and down direction and the vehicle dragging direction E, of the separating section 113 between the first dragging means 111 and the second dragging means 112, and a second detector 1532 at least partially arranged at the other side in the transverse direction of the separating section 113 between the first dragging means 111 and the second dragging means 112 and used for receiving beams emitted by the second radiation source 1522 and penetrating through the inspected vehicle, wherein the second radiation source 1522 is an X-ray beams accelerator or an X-ray beams machine.

As shown in FIG. 14, FIG. 15, FIG. 21 and FIG. 22, the vehicle inspection system further includes a transition means 235 arranged on the separating section 113 between the first dragging means 111 and the second dragging means 112, wherein the transition means 235 is used for supporting the vehicle when the vehicle moves from the first dragging means 111 to the second dragging means 112. See FIG. 2, FIG. 3, FIG. 4 and FIG. 8, the transition means 235 can include a platform 12, an overturning plate 13, a pedal 15 or other suitable supporting means or brackets.

See FIG. 14, FIG. 15, FIG. 19, FIG. 21 and FIG. 22, the vehicle inspection system further includes a linear cantilever crane structure arranged near the ground of the inspection passage 101 and serving as a first detector cantilever crane structure 116, wherein the first detector 1531 is arranged on the linear cantilever crane structure; moreover, at least a part of the linear cantilever crane structure is arranged near the ground of the separating section 113 between the first dragging means 111 and the second dragging means 112. The linear cantilever crane structure can be entirely located below the ground of the inspection passage, or the linear cantilever crane structure can be arranged below the transition means 235.

Alternatively, see FIG. 14, FIG. 15, FIG. 19, FIG. 21 and FIG. 22, the vehicle inspection system further includes a U-shaped cantilever crane structure serving as the first detector cantilever crane structure 116, wherein the U-shaped cantilever crane structure includes a substantially horizontal cantilever crane structure 1161 and two substantially vertical cantilever crane structures 1162 extending upwards from the two ends of the substantially horizontal cantilever crane structure, the substantially horizontal cantilever crane structure is arranged near the ground of the inspection passage 101, and the first detector 1531 is arranged on the substantially horizontal cantilever crane structure and the substantially vertical cantilever crane structures; moreover, at least a part of the substantially horizontal cantilever crane structure is arranged near the ground of the separating section 113 between the first dragging means 111 and the second dragging means 112. The substantially horizontal cantilever crane structure can be arranged below the transition means 235 or below the ground of the inspection passage. The substantially vertical cantilever crane structures can be vertical to the ground of the inspection passage and are located at the two sides of the inspection passage.

Figure 18:
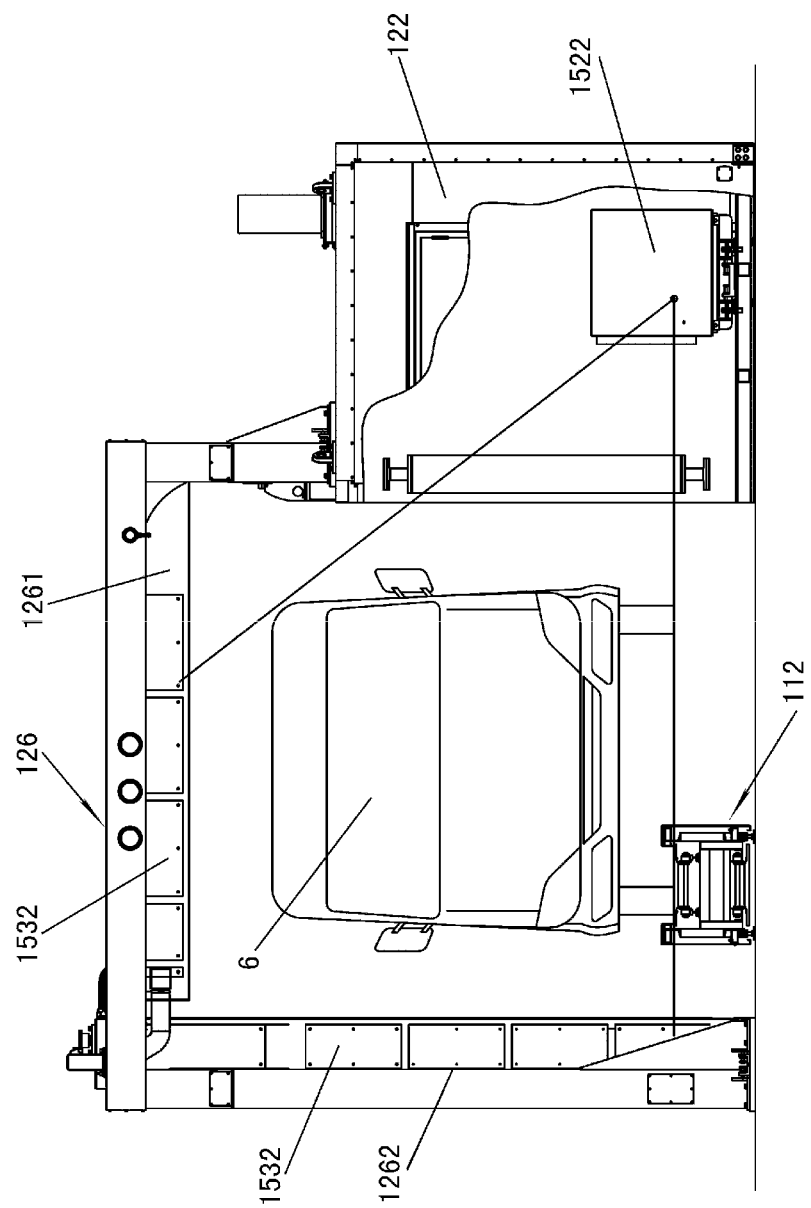
FIG. 18 is a schematic front view of a vehicle inspection system according to an embodiment of the present invention, wherein a radiation source arranged at one of the left side and the right side of an inspection passage is shown.
Figure 19:
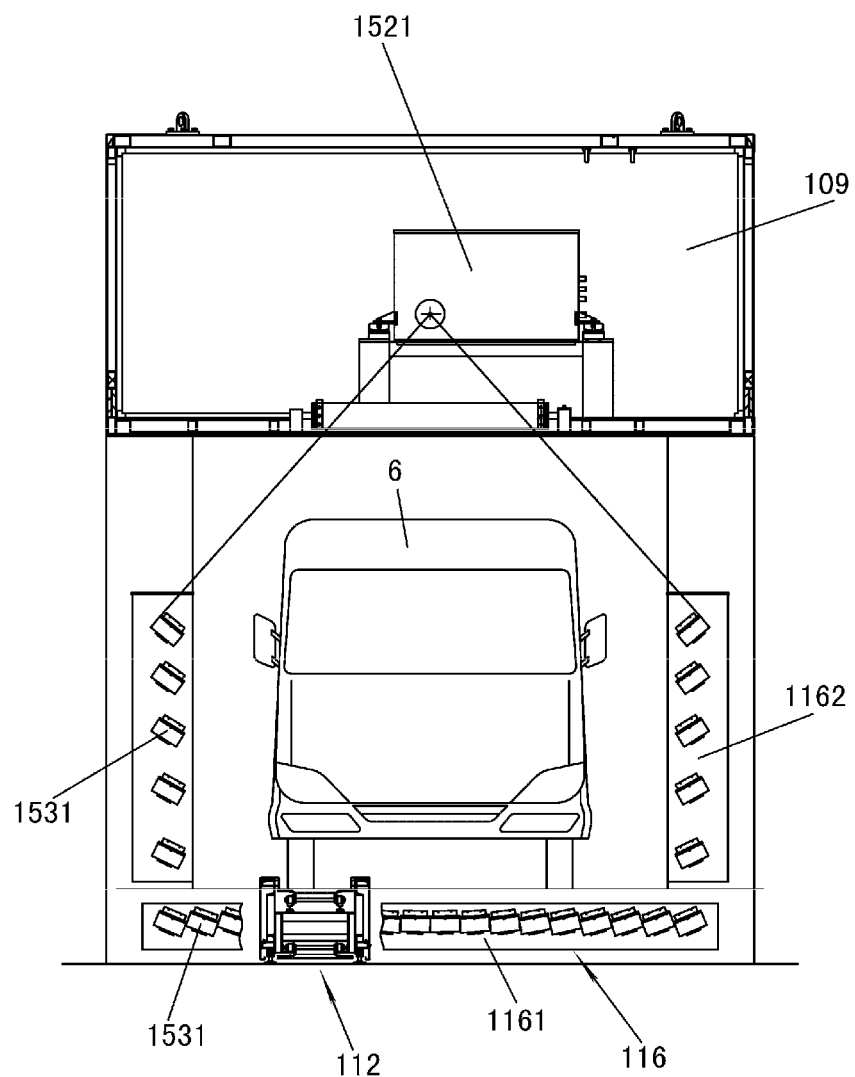
FIG. 19 is a schematic front view of a vehicle inspection system according to an embodiment of the present invention, wherein a radiation source arranged above an inspection passage is shown.

See FIG. 18, the vehicle inspection system further includes an L-shaped cantilever crane structure serving as a second detector cantilever crane 126, wherein the L-shaped cantilever crane structure includes a substantially horizontal cantilever crane structure and a substantially vertical cantilever crane structure extending upwards from the end of the substantially horizontal cantilever crane structure, the substantially horizontal cantilever crane structure is arranged near the ground of the inspection passage 101, and the substantially horizontal cantilever crane structure can be arranged below the transition means 235 or below the ground of the inspection passage. The second detector 1532 is arranged on the substantially horizontal cantilever crane structure and the substantially vertical cantilever crane structure; moreover, at least a part of the substantially horizontal cantilever crane structure is arranged near the ground of the separating section 113 between the first dragging means 111 and the second dragging means 112. The substantially vertical cantilever crane structure can be perpendicular to the ground of the inspection passage and is located at one side of the inspection passage.

Alternatively, see FIG. 18, the vehicle inspection system further includes an inverted L-shaped cantilever crane structure serving as the second detector cantilever crane 126, wherein the inverted L-shaped cantilever crane structure includes a substantially horizontal cantilever crane structure 1261 and a substantially vertical cantilever crane structure 1262 extending downwards from the end of the substantially horizontal cantilever crane structure, the substantially horizontal cantilever crane structure 1261 is arranged above the inspection passage 101, and the second detector 1532 is arranged on the substantially horizontal cantilever crane structure and the substantially vertical cantilever crane structure. The substantially horizontal cantilever crane structure can be arranged above the transition means 235. The substantially vertical cantilever crane structure can be perpendicular to the ground of the inspection passage and is located at one side of the inspection passage.

According to some embodiments of the present invention, the first detector 1531 and the second detector 1532 can be arranged in other manners, and the cantilever crane structure can also adopt other shapes.

In the vehicle inspection system according to the embodiment of the present invention, the vehicle can pass the inspection passage 101 under a first mode, a second mode or a third mode, under the first mode, the vehicle voluntarily passes the inspection passage 101, and the radiographic inspection system does not inspect the vehicle; under the second mode, the vehicle voluntarily passes the inspection passage 101, and the radiographic inspection system inspects the vehicle by adopting a dosage lower than a first preset value, wherein the dosage of the first preset value can be a maximal dosage harmless to human body and can also be a certain dosage below the maximal dosage; and under the third mode, the vehicle dragging system drags the vehicle to pass the inspection passage 101, and the radiographic inspection system inspects the vehicle by adopting a dosage larger than or equal to a second preset value, the second preset value can be the same as or different from the first preset value, and preferably, the second preset value is larger than the first preset value. Under the first mode and the second mode, the wheels on at least one side of the vehicle drive on the first dragging means 111 and the second dragging means 112, or the vehicle drives on a road beside the first dragging means 111 and the second dragging means 112.

Figure 21:
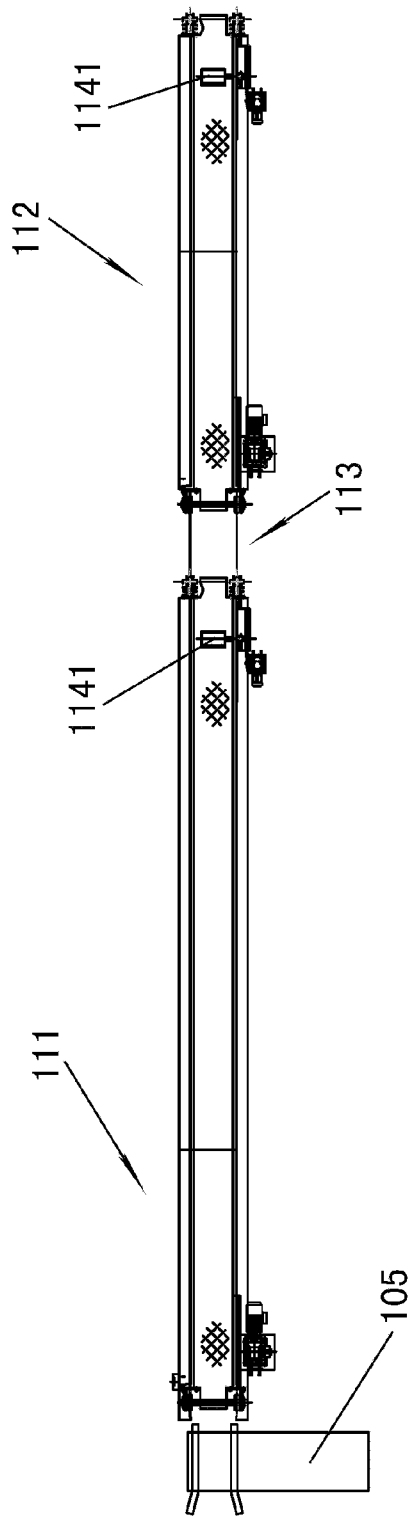
FIG. 21 is a schematic top view of a vehicle dragging system of a vehicle inspection system according to an embodiment of the present invention, wherein a dragging means of the vehicle dragging system includes a pushing roller.
Figure 22:
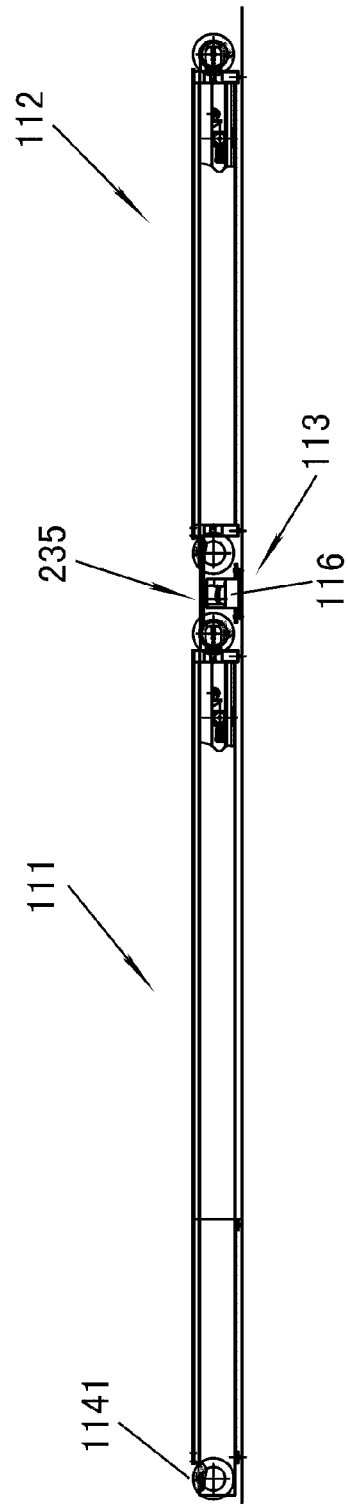
FIG. 22 is a schematic side view of a vehicle dragging system of a vehicle inspection system according to an embodiment of the present invention, wherein a dragging means of the vehicle dragging system includes a pushing roller.

As shown in FIG. 21 and FIG. 22, at least one of the first dragging means 111 and the second dragging means 112 includes two chains and a pushing roller connected between the two chains to serve as a pushing element 1141, wherein the pushing roller is used for pushing the wheels of the vehicle, in order to drive the vehicle to advance to pass the inspection passage 101.

Figure 15:
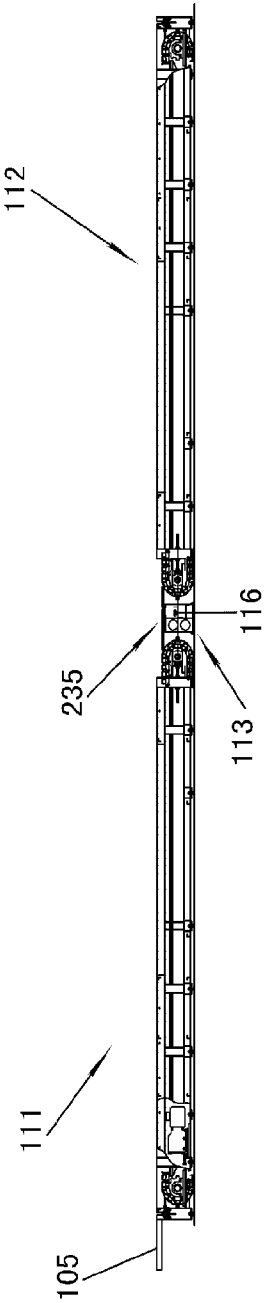
FIG. 15 is a schematic side view of a vehicle dragging system of a vehicle inspection system according to an embodiment of the present invention, wherein a dragging means of the vehicle dragging system includes a plate link chain.
Figure 16:
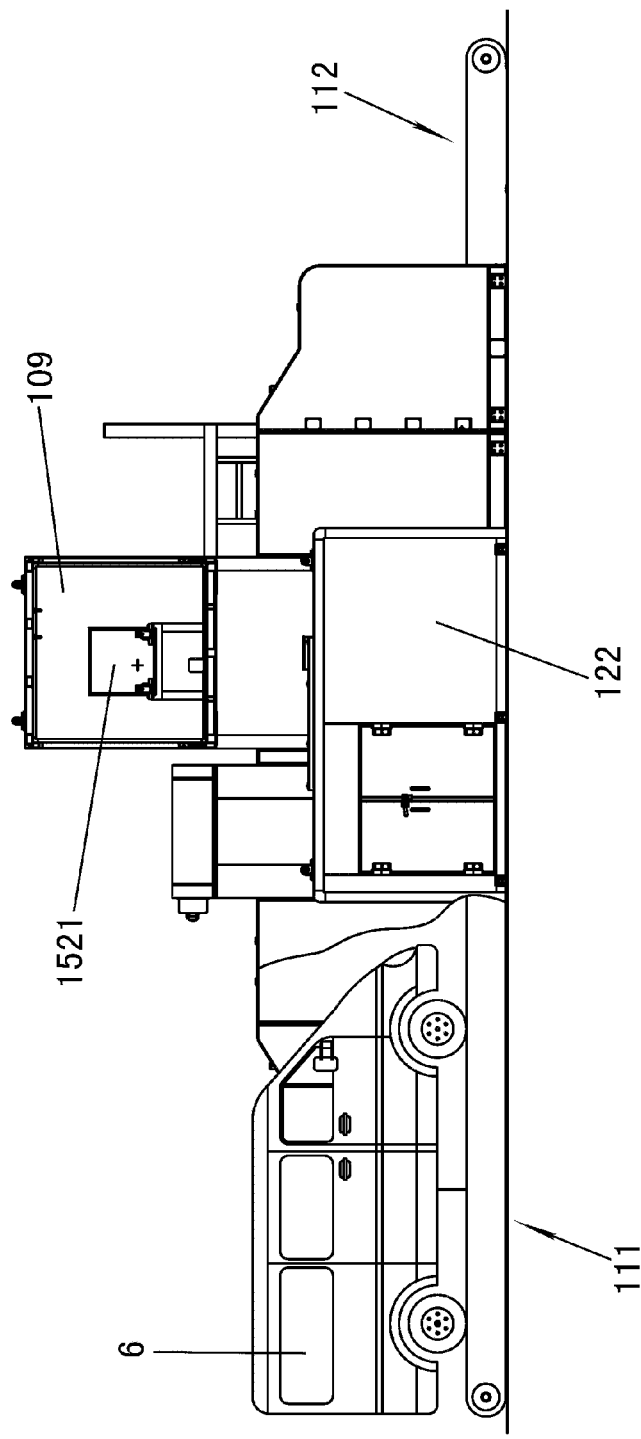
FIG. 16 is a schematic side view of a vehicle inspection system according to an embodiment of the present invention.

As shown in FIG. 14, FIG. 15 and FIG. 20, at least one of the first dragging means 111 and the second dragging means 112 includes a plate link chain 114 (an example of a elongated traction element). The plate link chain 114 includes a projection serving as the pushing element 1141, wherein the pushing element is used for pushing the wheels of the vehicle, in order to drive the vehicle to advance to pass the inspection passage 101.

According to the embodiment of the present invention, at least one of the first dragging means 111 and the second dragging means 112 drives the vehicle to advance to pass the inspection passage 101 through at least one wheel of the vehicle. The pushing element pushes at least one wheel of the vehicle, in order to drive the vehicle to advance to pass the inspection passage 101.

As shown in FIG. 14, the vehicle inspection system further includes a third dragging means 110 substantially parallel to the first dragging means 111, for enabling the first dragging means 111 and the third dragging means 110 to respectively drive the left and right wheels of the vehicle. The end of the third dragging means 110 adjacent to the separating section 113 can be substantially aligned to the end of the first dragging means 111 adjacent to the separating section 113. The third dragging means 110 is an auxiliary dragging means.

As shown in FIG. 14, the vehicle inspection system according to the embodiment of the present invention can further include an entrance guide rail and a guide platform 105. The first dragging means 111 and the second dragging means 112 can be used for dragging a single wheel or double wheels of the vehicle, in order to transfer the vehicle. When the vehicle drives on the first dragging means 111, the entrance guide rail and the guide platform 105 correctly guide the vehicle travelling direction and correct the deviation of the rear wheel.

As shown in FIG. 14, the third dragging means 110 is used for assisting in pushing the vehicle, when the vehicle transits from the first dragging means 111 to the second dragging means 112.

As shown in FIG. 14, the vehicle inspection system according to the embodiment of the present invention can further include a wheel blocking means 103 located at the right side of the first dragging means 111, for blocking the rear wheel when the vehicle move towards a direction reverse to the travelling direction.

As shown in FIG. 16, FIG. 17, FIG. 18 and FIG. 19, the vehicle inspection system includes a top radiation source cabin 109 provided with the first radiation source 1521, a side radiation source bin 122 provided with the second radiation source 1522, the first detector cantilever crane 116, the second detector cantilever crane 126, a radiogen detecting system 127, radiation shield walls 70, a computer, electric control equipment, imaging software and a sensor.

As shown in FIG. 16, FIG. 17, FIG. 18 and FIG. 19, the top radiation source cabin 109 is located above the cantilever crane and is used for placing the first radiation source 1521 and power distribution equipment; the side radiation source bin 122 is located on one side of the passage and is used for placing the second radiation source 1522 and power distribution equipment.

Figure 17:
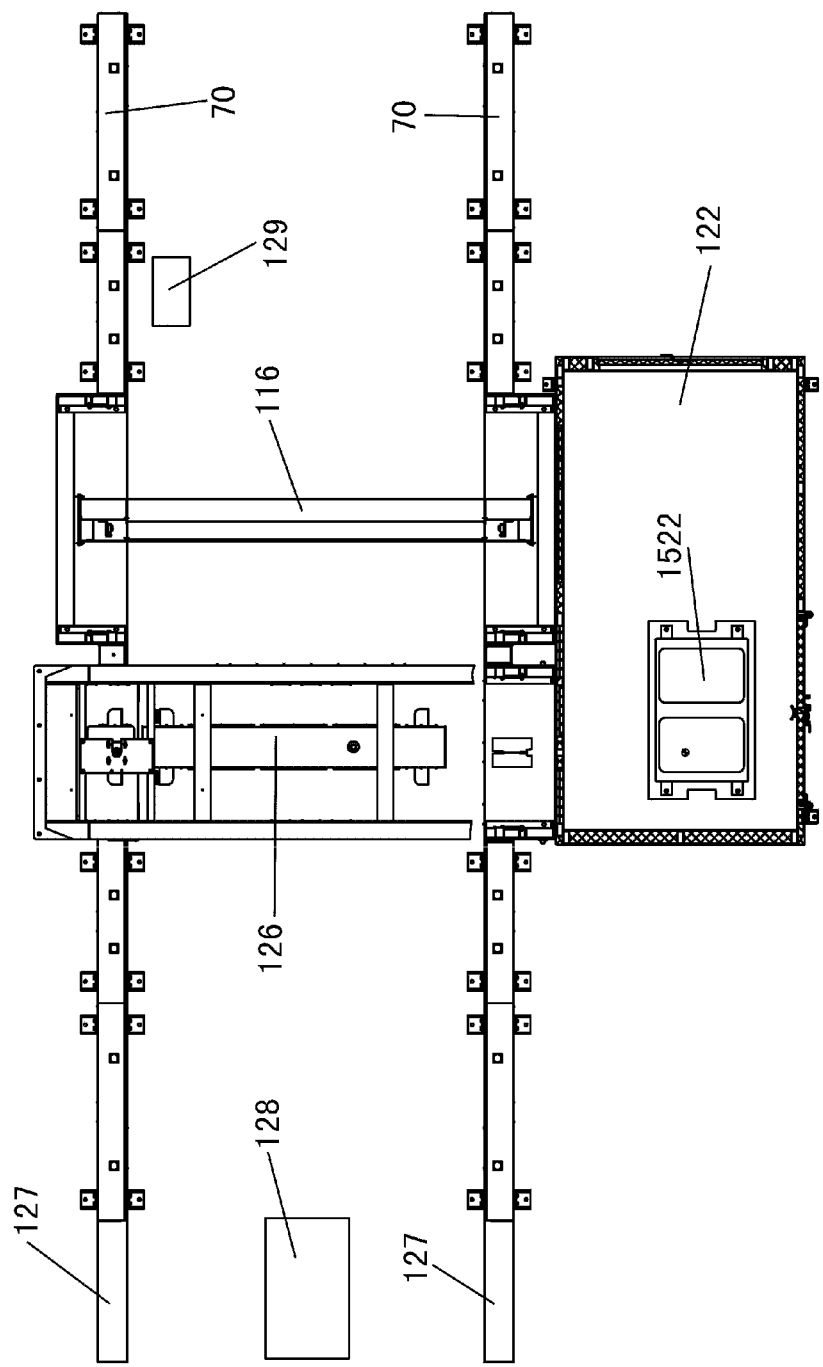
FIG. 17 is a schematic top view of a vehicle inspection system according to an embodiment of the present invention.

As shown in FIG. 17, the vehicle inspection system according to the present invention can include a radiogen monitoring system, an automatic license plate identification system and a chassis camera system, which are used for monitoring the existence of radiogen when performing radiation imaging inspection on the vehicle, identifying the license plate, automatically shooting the chassis and binding with the currently generated vehicle image, for retrospect.

When the vehicle is scanned, the vehicle drives on the first dragging means 111, after the rear wheel of the vehicle drives on the first dragging means 111, the system indicates the driver to stop through a traffic light, then the driver leaves the vehicle, after confirming that the driver leaves the vehicle, the first dragging means 111 is started, at this time, the first dragging means 111 pushes the wheels to move through the pushing element 1141, when the vehicle approaches to the beam flow center 106 of the ray beam, the radiation source is controlled to begin to emit X rays, and the detector in a detector arm receives the beams and converts the beams into necessary image data. The first dragging means 111 continues to push the vehicle to advance and transfers the vehicle to the second dragging means 112, the second dragging means 112 continues to push the wheel to advance through the pushing element 1141, such that the entire vehicle passes the beam flow center 106, at this time, the system performs related inspection on the generated radiation image of the vehicle. When detecting that the vehicle completely passes the beam flow center, a radiation source beam emission stop command is sent. However, at this time, the second dragging means 112 does not stop to transmitting the vehicle until pushing the rear wheel of the vehicle away from the second dragging means 112, and the dragging system resets to the initial position to wait for the next inspected vehicle to drive in.

In order to ensure the stable speed of the vehicle in the transfer process, the third dragging means 110 will assist the first dragging means 111 to stably transfer the vehicle and stably transfer the vehicle onto the second dragging means 112.

The vehicle inspection system according to the present invention can operate under a vehicle driving mode. Under the premise of the allowance of the local law, radiation imaging under the mode can be achieved. After the system is ready, the driver is instructed to drive into the passage through the traffic light, at this time, after the driver drives the vehicle to enter the inspection passage 101, the vehicle speed is measured through a speed sensor, in order to determine the beam emission frequency of the radiation sources 1521 and 1522 or the sampling frequency of the detector. When the vehicle approaches to the beam flow center 106 of the ray beams of the radiation source 1521 or 1522, the radiation sources 1521 and 1522 are respectively controlled to emit beams to scan the vehicle, in order to generate an X-ray beams image of the vehicle. After the vehicle leaves the beam flow center 106, the system sends a radiation source beam emission stop command, and the radiation sources stop emitting beams.

For an imaging system with an accelerator as the radiation source, the beam emission frequency of the accelerator is determined through the measured vehicle speed. For an imaging system with an X-ray beams machine as the radiation source, the sampling frequency of the detector is determined through the measured vehicle speed.

According to the embodiment of the present invention, the vehicle inspection system can further include a vehicle identification system used for identifying the type of the vehicle, in order to adopt a corresponding scanning inspection strategy according to the type of the vehicle. In addition, according to the embodiment of the present invention, the vehicle inspection system can further include a license plate identification system 129 for identifying the license plate number of the vehicle. According to the embodiment of the present invention, the vehicle inspection system can further include a chassis camera system 128 for shooting the chassis of the vehicle. The chassis camera system is installed on the ground of the inspection passage 101 or beneath the ground of the inspection passage 101.

Specifically, the vehicle inspection system according to the present invention can be provided with the radiogen detecting system and the license plate identification system. When the system performs the radiation imaging inspection on the vehicle, the radiogen detecting system 127 and the license plate identification system 129 installed at the two sides of the inspection passage 101 and the chassis camera system 128 installed on the ground or beneath the ground of the inspection passage 101 simultaneously detect whether radiogen exists in the vehicle 111, automatically identify the license plate of the vehicle, automatically shoot the chassis of the vehicle and associate the processing result with the image generated by current radiation scanning, for retrospect.

Although the chain and the plate link chain serving as the elongated traction element are described, the elongated traction element in the present invention can be any suitable elongated traction element, for example, a belt and the like.

Although some embodiments of the general idea of the patent have been shown and illustrated, it will be understood by those of ordinary skilled person in the art that, variations can be made on these embodiments without departing from the principle and spirit of the general idea of the patent, and the scope of the present invention is limited by the claims and their equivalents.

The invention claimed is:

1. A vehicle inspection system, comprising:
   a radiation source;
   an inspection passage enabling a vehicle to pass;
   a dragging system comprising a first dragging means and a second dragging means, which are sequentially arranged along a vehicle dragging direction; in the vehicle dragging direction, the first dragging means is arranged at the upstream of the second dragging means, and a separating section is arranged between the first dragging means and the second dragging means, so that the first dragging means is separated from the second dragging means by a preset distance in the vehicle dragging direction; and
   the first and second dragging means both include a supporting plate, an elongated traction element and a pushing element connected with the elongated traction element, the elongated traction elements of the first and second dragging means are continuous and integrated, thus the elongated traction elements and pushing elements extends on the separating section; the supporting plates of the first and second dragging means are separated and two pieces type, and no supporting plate is provided on the separating section; and the vehicle inspection system has a first mode, a second mode and a third mode:

under the first mode, the vehicle voluntarily passes the inspection passage, and the radiographic inspection system does not inspect the vehicle, under the second mode, the vehicle voluntarily passes the inspection passage, and the radiographic inspection system inspects the vehicle by adopting a dosage lower than a first preset value, and under the third mode, the dragging system drags the vehicle to pass the inspection passage, and the radiographic inspection system inspects the vehicle by adopting a dosage larger than or equal to a second preset value.

2. A vehicle inspection system according to claim 1 wherein said radiation source providing X-ray beams for scanning a vehicle and further comprising:

a detector used for receiving the X-ray beams emitted from the radiation source;

a scanning means frame being arranged within the range of the inspection passage, the radiation source is arranged at the top of the scanning means frame for scanning the vehicle passing the inspection passage, and the detector is arranged at a position opposite to the radiation source;

at least a part of paths of the beams of the radiation source passes through the separating section between the first dragging means and the second dragging means.

3. The vehicle inspection system of claim 2, further comprising:

the dragging means is arranged on the ground at one side within the range of the inspection passage, and is able to drag the vehicle which is driving into the inspection passage to pass the inspection passage.

4. The vehicle inspection system of claim 3, wherein the width of the inspection passage is arranged in such a manner that the vehicle is able to pass the inspection passage by means of the dragging means, and the vehicle is also able to pass the inspection passage along the ground provided with no dragging means.

5. The vehicle inspection system of claim 2, further comprising:

the radiation shield walls arranged at the two sides of the inspection passage a pedestrian passage arranged behind the radiation shield walls, for enabling a driver to walk from a starting point where the vehicle drives into the inspection passage to the destination where the vehicle is about to leave the inspection passage.

6. The vehicle inspection system according to claim 1, wherein said dragging system is arranged in the inspection passage; and further comprising:

a radiographic inspection system for inspecting a vehicle, wherein said radiation source is comprised in said radiographic inspection system, said radiation source for emitting beams of penetrating radiation and a detector for receiving the beams emitted by the radiation source and penetrating through the inspected vehicle;

at least a part of paths of the beams of the radiographic inspection system passes through the separating section between the first dragging means and the second dragging means.

7. The vehicle inspection system of claim 6, wherein the pushing element is used for pushing wheels to move so as to drive the vehicle to advance.

8. The vehicle inspection system of claim 6, wherein the radiation source is arranged above the inspection passage.

9. The vehicle inspection system of claim 6, further comprising a driving passage arranged in the inspection passage and used for enabling the vehicle to voluntarily pass, wherein the driving passage is arranged to be substantially parallel to the dragging means.

10. The vehicle inspection system of claim 6, further comprising a controller, wherein the controller corrects an acquired image of the inspected vehicle according to a scanned image acquired by the vehicle inspection system during no load of the dragging means, in order to remove the image of the dragging means from the acquired image of the inspected vehicle.

11. The vehicle inspection system of claim 10, wherein the controller corrects the acquired image of the inspected vehicle according to the position relationship of the inspected vehicle and at least one of the elongated traction element and the pushing element along the vehicle transfer direction, in order to remove the image of at least one of the elongated traction element and the pushing element from the acquired image of the inspected vehicle.

12. The vehicle inspection system of claim 10, wherein the pushing element of the dragging means contacts the wheels of the vehicle and pushes the wheels, in order to determine the position relationship of the inspected vehicle and at least one of the elongated traction element and the pushing element along the vehicle transfer direction.

13. The vehicle inspection system of claim 10, further comprising:

a position detecting means for detecting whether the pushing element arrives at a preset position, and sending a signal to the controller when the pushing element pushing the wheels of the vehicle or the pushing element during no load of the dragging means arrives at the preset position, in order to start the radiographic inspection system to scan the vehicle or the no-load dragging means.

14. The vehicle inspection system of claim 13, wherein the position detecting means is an optical transceiver, the optical transceiver is arranged at one side of the dragging means and emits a light beam towards one side of the dragging means, when the light beam irradiates a reflector at the end part of the pushing element, the optical transceiver receives the light beam reflected by the reflector at the end part of the pushing element, in order to determine that the pushing element arrives at the preset position.

15. The vehicle inspection system of claim 6, further comprising a controller, wherein the controller corrects an acquired image of the inspected vehicle according to a scanned image acquired by the vehicle inspection system during no load of the dragging means, in order to remove the image of at least one of the elongated traction element and the pushing element from the acquired image of the inspected vehicle.

16. The vehicle inspection system of claim 6, wherein the first dragging means comprises a first elongated traction element and a first pushing element connected with the first elongated traction element, and the first pushing element for pushing the wheels to move so as to drive the vehicle to advance;

the second dragging means comprises a second elongated traction element and a second pushing element connected with the second elongated traction element, and the second pushing element for pushing the wheels to move so as to drive the vehicle to advance.

17. The vehicle inspection system of claim 6, wherein the elongated traction element is a chain or a plate link chain.

18. The vehicle inspection system of claim 1, wherein under the first mode and the second mode, the wheels of at least one side of the vehicle drive on the first dragging means and the second dragging means or the vehicle drives on a road beside the first dragging means and the second dragging means.

19. The vehicle inspection system of claim 1, wherein the pushing element for pushing the wheels to move so as to drive the vehicle to advance,
the vehicle inspection system further comprises a driving passage arranged in the inspection passage and used for enabling the vehicle to voluntarily pass, and the driving passage is arranged to be substantially parallel to the dragging means, and
under the first mode, the vehicle voluntarily passes the inspection passage.

\* \* \* \* \*